(12) United States Patent
Takai et al.

(10) Patent No.: US 7,709,242 B2
(45) Date of Patent: May 4, 2010

(54) L-TYROSINE PRODUCING BACTERIUM AND A METHOD FOR PRODUCING L-TYROSINE

(75) Inventors: Atsuko Takai, Kawasaki (JP); Ranko Nishi, Kawasaki (JP); Yuji Joe, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/337,016

(22) Filed: Dec. 17, 2008

(65) Prior Publication Data

US 2009/0104683 A1    Apr. 23, 2009

Related U.S. Application Data

(62) Division of application No. 11/149,349, filed on Jun. 10, 2005, now Pat. No. 7,482,140.

(30) Foreign Application Priority Data

Jun. 15, 2004  (JP)  ............... 2004-176797
Apr. 8, 2005   (JP)  ............... 2005-112484

(51) Int. Cl.
*C12N 1/20* (2006.01)

(52) U.S. Cl. .................. 435/252.3; 435/108; 435/243; 435/252.33; 435/71.1; 435/69.1

(58) Field of Classification Search ....................... None
See application file for complete search history.

(56) References Cited

U.S. PATENT DOCUMENTS

| | | | |
|---|---|---|---|
| 4,681,852 A | 7/1987 | Tribe et al. | |
| 7,097,999 B2 | 8/2006 | Tsujimoto et al. | |
| 7,205,132 B2 | 4/2007 | Hirano et al. | |
| 7,300,776 B2 | 11/2007 | Ito et al. | |
| 7,335,496 B2 | 2/2008 | Yamamoto et al. | |
| 7,344,874 B2 | 3/2008 | Hara et al. | |
| 2002/0160461 A1 | 10/2002 | Nakai et al. | |
| 2003/0077764 A1 | 4/2003 | Tsujimoto et al. | |
| 2004/0121428 A1 | 6/2004 | Sugimoto et al. | |
| 2006/0019355 A1 | 1/2006 | Ueda et al. | |
| 2006/0141588 A1 | 6/2006 | Nakamura et al. | |
| 2006/0160191 A1 | 7/2006 | Kataoka et al. | |
| 2006/0205043 A1 | 9/2006 | Tsujimoto et al. | |
| 2006/0216796 A1 | 9/2006 | Hashiguchi et al. | |
| 2007/0004014 A1 | 1/2007 | Tsuji et al. | |
| 2007/0172932 A1 | 7/2007 | Hirano et al. | |

FOREIGN PATENT DOCUMENTS

EP    0 190 921    8/1986
EP    0 263 515    8/1987
WO    WO87/00202   1/1987

OTHER PUBLICATIONS

Greenspan et al (Nature Biotechnology 7: 936-937, 1999).*
Chothia et al (The EMBO Journal, 1986, 5/4:823-26).*
Champney, W. S., et al., "The Enzymology of Prephenate Dehydrogenase in *Bacillus subtilis*," J. Biol. Chem. 1970;245(15):3763-3770.
Chen, S., et al., "Mapping of chorismate mutase and prephenate dehydrogenase domains in the *Escherichia coli* T-protein," Eur. J. Biochem. 2003;270:757-763.
Christendat, D., et al., "Use of site-Directed Mutagenesis To Identify Residues Specific for Each Reaction Catalyzed by Chorismate Mutase-Prephenate Dehydrogenase from *Escherichia coli*," Biochem. 1998;37:15703-15712.
Christopherson, R. I., et al., "Chorismate Mutase-Prephenate Dehydrogenase from *Escherichia coli*: Positive Cooperativity with Substrates and Inhibitors," Biochem. 1985;24:1116-1121.
Cohen, G. N., et al., "Kinetics of Incorporation of p-Fluorophenylalanine by a Mutant of *Escherichia coli* Resistant to This Analogue," J. Bacteriol. 1958;76(3):328-330.
Lobocka, M., et al., "Organization and Expression of the *Escherichia coli* K-12 *dad* Operon Encoding the Smaller Subunit of D-Amino Acid Dehydrogenase and the Catabolic Alanine Racemase," J. Bacteriol. 1994;176(5):1500-1510.
Lütke-Eversloh, T., et al., "Feedback Inhibition of Chorismate Mutase/Prephenate Dehydrogenase (TyrA) of *Escherichia coli*: Generation and Characterization of Tyrosine-Insensitive Mutants," Appl. Environ. Microbiol. 2005;71(11):7224-7228.
Mikayama, T., et al., "Molecular cloning and functional expression of a cDNA encoding glycosylation-inhibiting factor," Proc. Natl. Acad. Sci. USA 1993;90:10056-10060.
Rudiger, J., "Characteristics of the amino acids as components of a peptide hormone sequence," Peptide Hormones. Biol. Council, Jun. 1976, pp. 5-7.
Turnbull, J., et al., "Kinetic Studies on Chorismate Mutase-Prephenate Dehydrogenase from *Escherichia coli*: Models for the Feedback Inhibition of Prephenate Dehydrogenase by L-Tyrosine," Biochem. 1991;30:7783-7788.
Search Report for European Patent App. No. 05012932.9 (Dec. 7, 2005).

* cited by examiner

*Primary Examiner*—Jennifer E Graser
(74) *Attorney, Agent, or Firm*—Shelly Guest Cermak; Cermak Kenealy Vaidya & Nakajima LLP

(57) ABSTRACT

The present invention describes the production of L-tyrosine by culturing in a medium an *Escherichia* bacterium which has L-tyrosine-producing ability and which carries a mutant prephenate dehydrogenase which is desensitized to feedback inhibition by L-tyrosine, producing and accumulating L-tyrosine in the medium or in the bacterial cells, and collecting L-tyrosine from the medium or the bacterial cells.

6 Claims, 9 Drawing Sheets

ID

L-TYROSINE PRODUCING BACTERIUM AND A METHOD FOR PRODUCING L-TYROSINE

This application is a Divisional Patent Application under 35 U.S.C. §120 to U.S. patent application Ser. No. 11/149,349, filed on Jun. 10, 2005, now U.S. Pat. Ser. No. 7,482,140, which claimed priority under 35 U.S.C. §119 to Japanese Patent Application Nos. 2004-176797, filed Jun. 15, 2004, and 2005-112484, filed on Apr. 8, 2005, which are incorporated by reference. The Sequence Listing filed electronically herewith is also hereby incorporated by reference in its entirety (File Name: US-232D_Seq_List; File Size: 47 KB; Date Created: Dec. 17, 2008).

BACKGROUND OF THE INVENTION

1. Field of the Invention

The present invention relates to L-tyrosine-producing bacterium and a method for producing L-tyrosine by fermentation.

2. Brief Description of the Related Art

L-tyrosine is useful as a raw material or as a synthetic intermediate for pharmaceuticals. Conventional methods for producing L-tyrosine include extracting L-tyrosine from precipitates obtained during degradation of vegetable proteins, such as soybean proteins (JP07-10821 A), and producing L-tyrosine by fermentation using, for example, bacteria of the genus *Brevibacterium* (JP09-121872 A).

Bacteria of the genus *Brevibacterium* have an L-tyrosine biosynthetic pathway called the arogenate pathway, which produces arogenate from prephenate by prephenate aminotransferase, and then produces L-tyrosine from arogenate by arogenate dehydrogenase. Conventionally, L-tyrosine is produced by utilizing a bacterium of the genus *Brevibacterium*, since in this bacterium, the above-mentioned two enzymes are not inhibited when L-tyrosine is final product. However, growth of this bacterium is slow, and therefore productivity of L-tyrosine by this bacterium is low.

On the other hand, in the L-tyrosine biosynthetic pathway of *Escherichia coli*, prephenate is dehydrated by prephenate dehydrogenase (hereinafter, abbreviated to "PDH") into 4-hydroxyphenylpyruvic acid, from which L-tyrosine is synthesized by aromatic amino acid aminotransferase. A problem in producing L-tyrosine by fermentation using *Escherichia coli* is that PDH, a first enzyme in this L-tyrosine-synthetic pathway, is subject to strong feedback inhibition by L-tyrosine, even with a low concentration of L-tyrosine. To efficiently produce L-tyrosine using *Escherichia coli*, the desensitization of this feedback inhibition by L-tyrosine is necessary first and foremost.

As for L-tyrosine production by *Escherichia coli*, it has been reported that bacteria resistant to p-fluoro-tyrosine excrete L-tyrosine (J. Bacteriol. 1958 September; 76(3): 328), and it was also reported that bacteria resistant to β-2-thienyl-alanine (J. Bacteriol. 1958 September; 76(3): 326), and bacteria resistant to P-aminophenylalanine (J. Bacteriol. 1969 March; 97(3): 1234) excrete L-tyrosine. However, mutations carried by those bacteria were not specified, or were found to be in a gene other than the PDH gene, such as 3-deoxy-D-arabino-heptulosonate-7-phosphate synthase (DS) gene or the like. Therefore, neither L-tyrosine-producing bacterium carrying PDH which is desensitized to feedback inhibition, nor a mutation resulting in desensitization of feedback inhibition of PDH activity has been reported.

Although a strain of *Bacillus* bacterium in which feedback inhibition of PDH is desensitized was obtained from D-tyrosine-resistant strains (J. Biol. Chem. 1970 Aug. 10; 245 (15): 3763), no mention has been made as to whether the desensitization of this inhibition actually results in enhanced production of L-tyrosine. Furthermore, a specific site of the mutation has not been examined. Furthermore, the procedure to obtain a D-tyrosine-resistant strain was not applicable to *Escherichia coli*, because *Escherichia coli* is inherently resistant to D-tyrosine due to the presence of the dadA (D-amino acid dehydrogenase A) gene (J. Bacteriol. 1994 March; 176 (5): 1500).

In *Escherichia coli*, PDH is encoded by the tyrA gene and is identical to Chorismate mutase (CM) (SEQ ID NO: 1). It has been reported that PDH is inhibited by L-tyrosine at a concentration as low as 300 μM (Biochemistry. 1985 Feb. 26; 24(5): 1116). On the other hand, it was reported that the active sites of PDH are within the region of amino acids at positions 94 to 373, and that the region also includes sites involved in inhibition of its activity by L-tyrosine (Eur J Biochem. 2003 February; 270(4): 757). However, it has not been elucidated which amino acid residue is involved in the inhibition.

3-fluoro-tyrosine is known as an inhibitor of 3-deoxy-D-arabino-heptulosonate-7-phosphate synthase and has been used to isolate a tyrosine repressor (tyrR)-deficient strain. Although 3-fluoro-tyrosine is also known to inhibit PDH activity, the use of 3-fluoro-tyrosine to obtain a PDH mutant has not been reported to date.

SUMMARY OF THE INVENTION

An object of the present invention is to provide a novel L-tyrosine-producing bacterium belonging to the genus *Escherichia* and to provide a method for producing L-tyrosine using the *Escherichia* bacterium.

The inventors of the present invention extensively studied to arrive at the above-mentioned object, and as a result, it was found that an *Escherichia* bacterium harboring a mutant PDH which is desensitized to feedback inhibition by L-tyrosine can produce L-tyrosine efficiently and thereby, completed the present invention.

That is, the present invention provides the following:

It is an aspect of the present invention to provide an *Escherichia* bacterium which has L-tyrosine-producing ability comprising a mutant prephenate dehydrogenase which is desensitized to feedback inhibition by L-tyrosine.

It is an aspect of the present invention to provide the *Escherichia* bacterium as described above, wherein said mutant prephenate dehydrogenase comprises a protein in which one or more amino acids selected from the amino acids at positions 250 to 269 in a wild-type prephenate dehydrogenase is/are replaced by other amino acids.

It is an aspect of the present invention to provide the *Escherichia* bacterium as described above, wherein said mutant prephenate dehydrogenase comprises a protein in which an amino acid selected from the alanine at position 250, the glutamine at position 253, the alanine at position 254, the leucine at position 255, the histidine at position 257, the phenylalanine at position 258, the alanine at position 259, the threonine at position 260, the phenylalanine at position 261, the tyrosine at position 263, the leucine at position 265, the histidine at position 266, the leucine at position 267, the glutamic acid at position 269, and a combination thereof, is/are replaced by other amino acids.

It is an aspect of the present invention to provide the *Escherichia* bacterium as described above, wherein the alanine at position 250 is replaced by phenylalanine, the glutamine at position 253 is replaced by leucine, the alanine at position 254 is replaced by serine, proline, or glycine, the leucine at position 255 is replaced by glutamine, the histidine at position 257 is replaced by tyrosine, threonine, serine, alanine, or leucine, the phenylalanine at position 258 is replaced by cysteine, alanine, isoleucine, or valine, the alanine at position 259 is replaced by leucine, valine, or isoleucine, the threonine at position 260 is replaced by lycine, alanine, valine, cysteine, isoleucine, phenylalanine, asparagine, or serine, the phenylalanine at position 261 is replaced by methionine or leucine, the tyrosine at position 263 is replaced by cysteine, glycine, threonine, or methionine, the leucine at position 265 is replaced by lysine, isoleucine, tyrosine, or alanine, the histidine at position 266 is replaced by tryptophan or leucine, the leucine at position 267 is replaced by tyrosine or histidine, and the glutamic acid at position 269 is replaced by tyrosine, phenylalanine, glycine, isoleucine, or leucine.

It is an aspect of the present invention to provide the *Escherichia* bacterium as described above, wherein said wild-type prephenate dehydrogenase is selected from the group consisting of:

(a) an amino acid sequence of SEQ ID NO: 2; and (b) an amino acid sequence of SEQ ID NO: 2 including substitution, deletion or addition of one or several amino acids so long as said protein retains prephenate dehydrogenase activity.

It is an aspect of the present invention to provide the *Escherichia* bacterium as described above, wherein said *Escherichia* bacterium is further modified so that expression of a gene encoding a prephenate dehydratase is reduced.

It is an aspect of the present invention to provide the *Escherichia* bacterium as described above, wherein said *Escherichia* bacterium is further modified so that expression of a gene encoding a tyrosine repressor is reduced.

It is an aspect of the present invention to provide the *Escherichia* bacterium as described above, wherein said *Escherichia* bacterium further comprises a 3-deoxy-D-arabino-heptulosonate-7-phosphate synthase which is desensitized to inhibition by L-phenylalanine.

It is an aspect of the present invention to provide the *Escherichia* bacterium as described above, wherein said *Escherichia* bacterium is further modified so that expression of a gene encoding a shikimate kinase II is enhanced.

It is a further aspect of the present invention to provide a method for producing L-tyrosine comprising culturing the *Escherichia* bacterium as described above in a medium, and collecting L-tyrosine from the medium or the bacterium.

It is an aspect of the present invention to provide a method for producing L-tyrosine or a derivative thereof comprising culturing an *Escherichia* bacterium in a medium, and collecting L-tyrosine or a derivative thereof from the medium or the bacterium, wherein said *Escherichia* bacterium is modified so that expression of the genes encoding a prephenate dehydratase and a tyrosine repressor is reduced, and expression of genes encoding a prephenate dehydrogenase and a shikimate kinase II is enhanced, and wherein said bacterium harbors a 3-deoxy-D-arabino-heptulosonate-7-phosphate synthase which is desensitized to inhibition by L-phenylalanine.

It is an aspect of the present invention to provide a method of screening for a gene encoding a prephenate dehydrogenase which is desensitized to feedback inhibition by L-tyrosine comprising introducing a mutation into a gene encoding a wild-type prephenate dehydrogenase, introducing the mutated gene into a microorganism, selecting a microorganism having 3-fluorotyrosine resistance, and isolating a gene encoding a prephenate dehydrogenase which is desensitized to feedback inhibition by L-tyrosine from the selected microorganism.

DETAILED DESCRIPTION OF THE PREFERRED EMBODIMENTS

Figure 1:
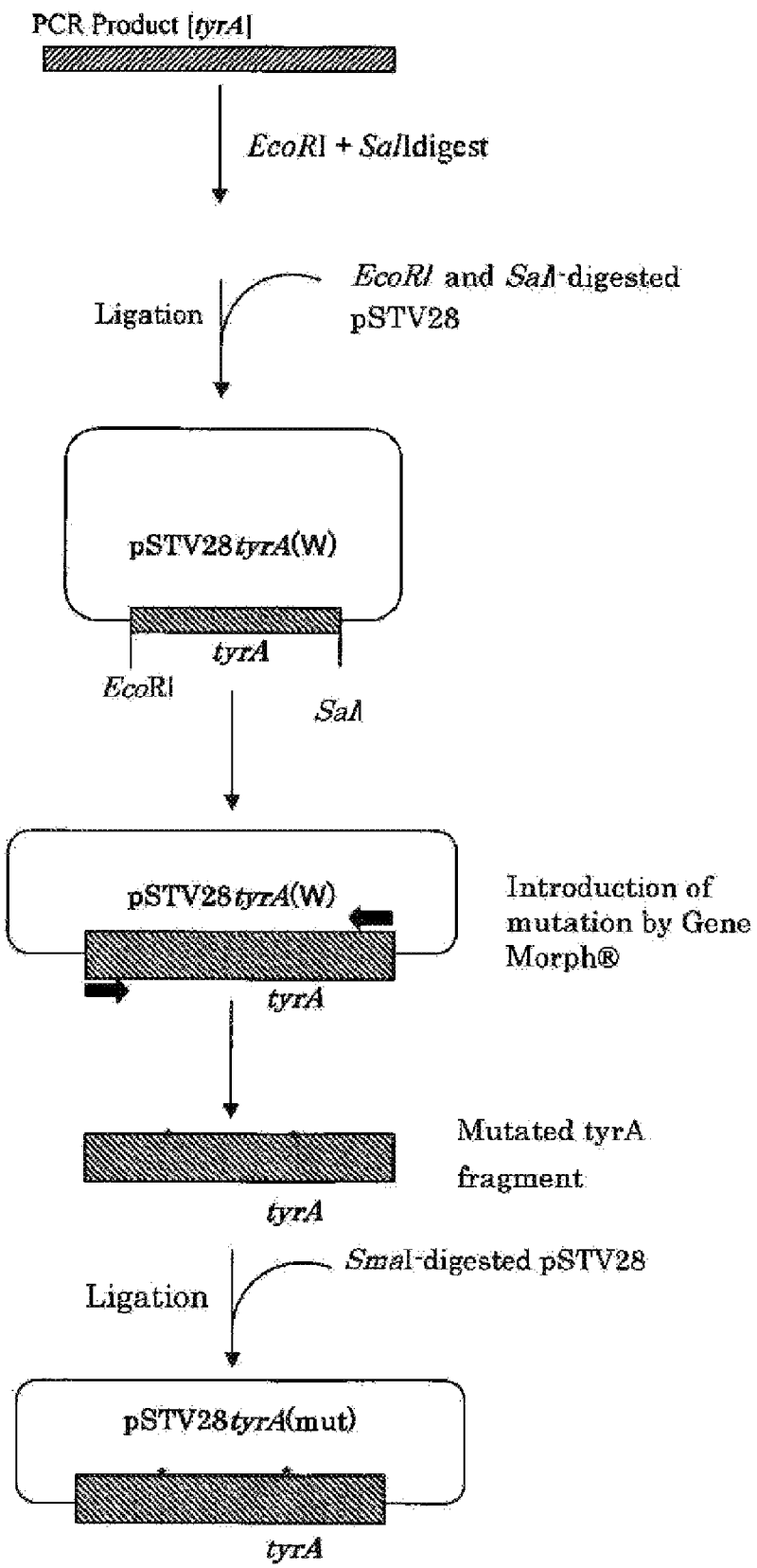
FIG. 1 shows the construction scheme of plasmid pSTV-tyrA(mut).

Hereinafter, the present invention will be described in detail.

<1> The *Escherichia* Bacterium of the Present Invention

The *Escherichia* bacterium of the present invention has an L-tyrosine-producing ability and harbors a mutant PDH which is desensitized to feedback inhibition by L-tyrosine.

The *Escherichia* bacterium that can be used to obtain the *Escherichia* bacterium of the present invention may be any of those described in the work of Neidhardt, F. C. et. al. (*Escherichia coli* and *Salmonella Typhimurium*, American Society for Microbiology, p 1208, Table 1), and for example, *Escherichia coli*. Examples of wild-type strains of *Escherichia coli* include K12 strain or a derivative thereof, *Escherichia coli* MG1655 strain (ATCC No. 47076), and W3100 strain (ATCC No. 27325). Those bacteria are available from, for example, the American Type Culture Collection (ATCC, Address: P.O. Box 1549, Manassas, Va. 20108, United States of America).

"The L-tyrosine-producing ability" refers to an ability to cause accumulation of a significant amount of L-tyrosine in a medium and/or an ability to increase the intracellular content of L-tyrosine, as compared to a wild-type strain or an unmutated strain. The *Escherichia* bacterium of the present invention may be a bacterium intrinsically having L-tyrosine-producing ability, or may be a bacterium modified to have L-tyrosine-producing ability. Furthermore, the *Escherichia* bacterium of the present invention may be a bacterium which gained L-tyrosine-producing ability by the introduction of a mutant PDH, or a mutant 3-deoxy-D-arabino-heptulosonate-7-phosphate synthase which is desensitized to feedback inhibition by L-phenylalanine.

In the present invention, "PDH" refers to a protein which has an activity of catalyzing dehydration of prephenate to produce 4-hydroxyphenylpyruvic acid. Wild-type PDH refers to a PDH which is sensitive to feedback inhibition by L-tyrosine. An example of such a protein is a protein having the amino acid sequence of SEQ ID NO: 2. A wild-type PDH may be a protein having the amino acid sequence of SEQ ID NO: 2, which includes a substitution, deletion, or addition of one or several amino acids, so long as it retains the above-described activity. "Several" as used herein is specifically from 2 to 20, preferably from 2 to 10, more preferably from 2 to 5. The "substitution" is a mutation which deletes at least one amino acid and inserts another amino acid at the same position in SEQ ID NO: 2. Amino acid substitutions, though not particularly limited as long as the above activity is maintained, are preferably the following substitutions: substitution of ser or thr for ala; substitution of gln his or lys for arg; substitution of glu, gln, lys, his or asp for asn; substitution of asn, glu or gln for asp; substitution of ser or ala for cys; substitution of asn, glu, lys, his, asp or arg for gln; substitution of asn, gln, lys or asp for glu; substitution of pro for gly; substitution of asn, lys, gln, arg or tyr for his; substitution of leu, met, val or phe for ile; substitution of ile, met, val or phe for leu; substitution of asn, glu, gln, his or arg for lys; substitution of ile, leu, val or phe for met; substitution of trp, tyr, met ile or leu for phe; substitution of thr or ala for ser; substitution of ser or ala for thr; substitution of phe or tyr for trp; substitution of his, phe or trp for tyr; and substitution of met, ile or leu for val.

Moreover, a wild-type PDH may have a homology of 80% or more, preferably 90% or more, especially preferably 95% or more to the amino acid sequence of SEQ ID NO: 2. as long as it retains the above-described activity.

Furthermore, a wild-type PDH may be encoded by a DNA having a nucleotide sequence of SEQ ID NO: 1 or by a DNA hybridizable to a DNA having a nucleotide sequence of SEQ ID NO: 1 under stringent conditions and having the above-described activity. Examples of stringent conditions used herein include: a condition of one time, preferably two or three times, of washing at salt concentrations corresponding to 1×SSC, 0.1% SDS at 65° C., preferably 0.1×SSC, 0.1% SDS at 65° C.

On the other hand, "mutant PDH which is desensitized to feedback inhibition by L-tyrosine" refers to, for example, a PDH which exhibits the activity in the presence of L-tyrosine to the same extent as the activity in the absence of L-tyrosine. For example, such mutant PDH refers to a PDH which exhibits the activity in the presence of 100 µM L-tyrosine, not less than 50%, preferably not less than 80%, more preferably not less than 90% of the activity in the absence of L-tyrosine. Such mutant PDH can be obtained by introducing amino acid substitutions into wild-type PDHs and selecting a PDH which is not subject to feedback inhibition by L-tyrosine due to the amino acid substitution-introduced PDHs. Specifically, nucleotide substitutions causing amino acid substitutions are introduced into a DNA encoding PDH (e.g., SEQ ID NO: 1) by the use of, for example, site-directed mutagenesis using PCR or the like, and an *Escherichia* bacterium, preferably an *Escherichia* bacterium in which a wild-type PDH gene is disrupted is transformed with the mutated DNA. The PDH activity of the bacterium is then measured in the presence and absence of L-tyrosine, and a strain in which PDH is resistant to feedback inhibition by L-tyrosine is selected. PDH activity can be measured according to the method described in Biochemistry. 1990 Nov. 6; 29(44): 10245-54.

A gene encoding PDH which is desensitized to feedback inhibition by L-tyrosine can also be obtained by using 3-fluorotyrosine according to the following procedures. Namely, mutations are introduced into a gene encoding a wild-type PDH, the mutated gene is introduced into a microorganism, a 3-fluorotyrosine-resistant strain is selected, the PDH activity of the selected strain is measured in the presence and absence of L-tyrosine to thereby select a strain harboring a mutant PDH which is desensitized to feedback inhibition by L-tyrosine, and finally a gene encoding the mutant PDH is isolated from the selected strain.

Mutant PDH carried by the *Escherichia* bacterium of the present invention is not particularly limited as long as feedback inhibition by L-tyrosine therein is desensitized. Preferable examples of the mutant PDH include those having an amino acid sequence of wild-type PDH whereby one or more amino acids selected from the amino acids at positions 250 to 269 are replaced by the other amino acids.

More preferable examples of the amino acids to be replaced include one or more amino acids selected from the alanine at position 250, the glutamine at position 253, the alanine at position 254, the leucine at position 255, the histidine at position 257, the phenylalanine at position 258, the alanine at position 259, the threonine at position 260, the phenylalanine at position 261, the tyrosine at position 263, the leucine at position 265, the histidine at position 266, the leucine at position 267, and the glutamic acid at position 269.

Although the types of amino acids which are used to replace the above amino acids are not particularly limited as long as the amino acid substitution generates mutant PDH which is desensitized to feedback inhibition by L-lysine, the following substitutions are preferable: substitution of phenylalanine for alanine at position 250; substitution of leucine for glutamine at position 253; substitution of serine, proline or glycine for alanine at position 254; substitution of glutamine for leucine at position 255; substitution of tyrosine, threonine, serine, alanine or leucine for histidine at position 257; substitution of cysteine, alanine, isoleucine or valine for phenylalanine at position 258; substitution of leucine, valine or isoleucine for alanine at position 259; substitution of glycine, alanine, valine, cysteine, isoleucine, phenylalanine, asparagine, or serine for threonine at position 260; substitution of methionine or leucine for phenylalanine at position 261; substitution of cysteine, glycine, threonine or methionine for tyrosine at position 263; substitution of lysine, isoleucine, tyrosine or alanine for leucine at position 265; substitution of tryptophan or leucine for histidine at position 266; substitution of tyrosine or histidine for leucine at position 267; and substitution of tyrosine, phenylalanine, glycine, isoleucine or leucine for glutamic acid at position 269.

The numbering of the amino acid positions as used herein represent the positions in the amino acid sequence shown in SEQ ID NO: 2. These positions may be shifted ahead or backward by the aforementioned deletion, insertion, addition or inversion of one or several amino acids. For example, if one amino acid residue is inserted into the upstream position, the threonine originally located at the position 260 shifts to position 261. In the present invention, such threonine equivalent to "the threonine at position 260" is also referred to as the "threonine at position 260." The same is true with regard to the other amino acid positions.

In order to introduce the above-mentioned mutant PDH into an *Escherichia* bacterium, the *Escherichia* bacterium may be transformed with, for example, a plasmid containing a DNA encoding the mutant PDH.

Although a DNA encoding a mutant PDH (also referred to as a mutant tyrA gene) is not particularly limited as long as it encodes a protein which has PDH activity and which is desensitized to feedback inhibition by L-threonine, examples of such DNA include a gene having a nucleotide sequence of SEQ ID NO: 1 or a nucleotide sequence able to hybridize with a polynucleotide having a nucleotide sequence of SEQ ID NO: 1 under stringent conditions, whereby a codon corresponding to one or more amino acids selected from the amino acids at positions 250 to 269 of SEQ ID NO: 2 is substituted by a codon corresponding to another amino acid.

Examples of vectors that can be used for introducing a mutant tyrA gene include a plasmid autonomously replicable in an *Escherichia* bacterium, and specifically include pUC19, pUC18, pHSG299, pHSG399, pHSG398, pACYC184, (pHSG and pACYC are available from Takara Bio Inc.), RSF1010, pBR322, and pMW219 (pMW is available from Nippon Gene Co., Ltd.).

The recombinant DNA containing the mutant tyrA gene prepared as described above can be introduced into an *Escherichia* bacterium by any known transformation method. Examples of transformation methods include treating recipient cells with calcium chloride so as to increase permeability of the DNA (Mandel, M. and Higa, A., J. Mol. Biol., 53, 159 (1970)), preparing competent cells from cells which are at the growth phase, followed by transformation with DNA (Duncan, C. H., Wilson, G. A. and Young, F. E., Gene, 1, 153 (1977)), and so forth.

The aforementioned mutant tyrA gene may also be integrated into a chromosomal DNA of the host bacterium. In order to integrate the gene into a chromosomal DNA of a bacterium, homologous recombination (Experiments in Molecular Genetics, Cold Spring Harbor Lab., 1972) may be carried out by targeting a sequence which exist in multiple copies on a chromosomal DNA. Repetitive DNA and inverted repeats at an end of a transposon can be used as a sequence which exists in multiple copies on a chromosomal DNA. Alternatively, as disclosed in EP0332488B, it is also possible to incorporate a target gene into a transposon, and allow it to be transferred so that multiple copies of the gene are integrated into the chromosomal DNA. Furthermore, a target gene may also be incorporated into a host chromosome by using Mu phage (EP0332488B).

Expression of the mutant tyrA gene may be controlled by the native promoter of the tyrA gene. Alternatively, the native promoter may be replaced with a stronger promoter such as the lac promoter, trp promoter, trc promoter, tac promoter, $P_R$ promoter or $P_L$ promoter of lambda phage, tet promoter, and amyE promoter.

As methods for preparation of chromosomal DNA, preparation of a chromosomal DNA library, hybridization, PCR, preparation of plasmid DNA, digestion and ligation of DNA, transformation, design of oligonucleotides used as primers and so forth, ordinary methods known to those skilled in the art can be employed. These methods are described in Sambrook, J., Fritsch, E. F. and Maniatis, T., "Molecular Cloning A Laboratory Manual, Second Edition", Cold Spring Harbor Laboratory Press, (1989) and so forth.

The *Escherichia* bacterium of the present invention is preferably an *Escherichia* bacterium harboring the above-mentioned mutant PDH and further modified so that expression of a gene encoding prephenate dehydratase is reduced. An example of a gene encoding prephenate dehydratase (also referred to as a pheA gene) is a gene having a nucleotide sequence of SEQ ID NO: 3. The gene encoding prephenate dehydratase may also be a gene which is able to hybridize with a polynucleotide having a nucleotide sequence of SEQ ID NO: 3 under stringent conditions as long as it encodes a protein having prephenate dehydratase activity. Examples of the stringent conditions used herein include: washing one time, preferably two or three times, at salt concentrations corresponding to 1×SSC, 0.1% SDS at 65° C., preferably 0.1×SSC, 0.1% SDS at 65° C. Prephenate dehydratase activity can be measured according to a method described in Biochemica Biophysica Acta (BBA) 1965 (100) 76-88. It is preferred that the expression of a pheA gene is reduced to 10% or less as compared to that of unmodified strains, such as a wild-type strain. Expression of the pheA gene can be confirmed by measuring the amount of mRNA transcribed from the pheA gene in the bacterial cells by northern hybridization or RT-PCR. In the present invention, reduction of a pheA gene expression includes complete loss of expression. A modification to reduce the expression of a pheA gene can be carried out by gene disruption or alteration of an expression regulatory region such as a promoter. Specifically, such modification can be carried out by the method described below.

Gene disruption by homologous recombination has already been established, and examples thereof include a method using a linear DNA and a method using a plasmid containing a temperature-sensitive replication origin. An example of a plasmid containing a temperature-sensitive replication origin for *Escherichia coli* is pMAN031 (Yasueda, H. et al., Appl. Microbiol. Biotechnol., 36, 211 (1991)), pMAN997 (WO 99/03988), and pEL3 (K. A. Armstrong et. al., J. Mol. Biol. (1984) 175, 331-347).

A pheA gene on a host chromosome can be replaced with a deletion-type pheA gene in which part of its internal sequence is deleted, for example, as follows. That is, a recombinant DNA is prepared by inserting a temperature-sensitive replication origin, a deletion-type pheA gene, and a marker gene conferring resistance to a drug such as ampicillin or chloramphenicol into a vector, and an *Escherichia* bacterium is transformed with the recombinant DNA. Furthermore, the resulting transformant strain is cultured at a temperature at which the temperature-sensitive replication origin does not function, and then the transformant strain is cultured in a medium containing the drug to obtain a transformant strain in which the recombinant DNA is incorporated into the chromosomal DNA.

In a strain in which the recombinant DNA is incorporated into the chromosomal DNA as described above, the deletion-type pheA gene is recombined with the pheA gene originally present on the chromosome, and the two fusion genes of the chromosomal pheA gene and the deletion-type pheA gene are inserted into the chromosome so that the other portions of the recombinant DNA (vector segment, temperature-sensitive replication origin, and drug resistance marker) are present between the two fusion genes.

Then, in order to leave only the deletion-type pheA gene on the chromosomal DNA, one copy of the pheA gene is eliminated together with the vector segment (including the temperature-sensitive replication origin and the drug resistance marker) from the chromosomal DNA by recombination of two of the pheA genes. In this case, the normal pheA gene is left on the chromosomal DNA and the deletion-type pheA gene is excised from the chromosomal DNA, or to the contrary, the deletion-type pheA gene is left on the chromosomal DNA and the normal pheA gene is excised from the chromosome DNA. In both cases, the excised DNA may be harbored in the cell as a plasmid when the cell is cultured at a temperature at which the temperature-sensitive replication origin can function. Subsequently, if the cell is cultured at a temperature at which the temperature-sensitive replication origin cannot function, the pheA gene on the plasmid is eliminated along with the plasmid from the cell. Then, a strain in which pheA gene is disrupted can be obtained by selecting a strain in which the deletion-type pheA gene is left on the chromosome using PCR, Southern hybridization or the like.

By the way, a tyrosine repressor suppresses expression of the tyrA gene, or the like (J. Biol. Chem., 1986, vol. 261, p 403-410). Thus, the bacterium of the present invention may be an *Escherichia* bacterium further modified to reduce the expression of a gene encoding a tyrosine repressor. Examples of a gene encoding a tyrosine repressor (also referred to as a tyrR gene) include a gene having a nucleotide sequence of SEQ ID NO: 5. A gene encoding a tyrosine repressor may also be a gene which is able to hybridize with a polynucleotide having a nucleotide sequence of SEQ ID NO: 5 under stringent conditions as long as it encodes a protein having tyrosine repressor activity. Examples of the stringent conditions used herein include: washing one time, preferably two or three times, at salt concentrations corresponding to 1×SSC, 0.1% SDS at 65° C., preferably 0.1×SSC, 0.1% SDS at 65° C. It is preferred that the expression of a tyrR gene is decreased to 10% or less as compared to that of unmodified strains such as a wild-type strain. In the present invention, reduction of a tyrR gene expression includes complete loss of the expression. A modification for reducing the expression of a tyrR gene can be carried out by gene disruption or alteration of an expression regulatory region such as a promoter. Specifically, this modification can be carried out in the same manner as in the disruption of the pheA gene as described above.

The bacterium of the present invention may be a bacterium which further comprises 3-deoxy-D-arabino-heptulosonate-7-phosphate synthase (also referred to as DS) which is desensitized to feedback inhibition by L-phenylalanine. Examples of DS which is desensitized to feedback inhibition by L-phenylalanine include a protein having an amino acid sequence of wild-type DS (e.g., SEQ ID NO: 8) encoded by aroG gene (e.g., SEQ ID NO: 7) whereby the proline at position 150 is replaced by leucine; a protein having an amino acid sequence of wild-type DS whereby alanine at position 202 is replaced by threonine; a protein having an amino acid sequence of wild-type DS whereby asparatic acid at position 146 is replaced by asparagine; a protein having an amino acid sequence of wild-type DS whereby methionine at position 147 is replaced by isoleucine and glutamic acid at position 332 is replaced by lysine; a protein having an amino acid sequence of wild-type DS whereby methionine at position 147 is replaced by isoleucine; and a protein having an amino acid sequence of wild-type DS whereby methionine at position 157 is replaced by isoleucine and alanine at position 219 is replaced by threonine (see JP 05-344881 A or JP 05-236947 A). A gene encoding either of these proteins is introduced into an *Escherichia* bacterium to obtain the *Escherichia* bacterium carrying DS which is desensitized to feedback inhibition by L-phenylalanine. Introduction of the gene can be carried out in the same way as the introduction of the mutant tyrA gene as described above.

The bacterium of the present invention may be further modified to increase the expression of a gene encoding shikimate kinase (aroL). An example of a gene encoding shikimate kinase is a gene having a nucleotide sequence of SEQ ID NO: 9. A gene encoding shikimate kinase may also be a gene which is able to hybridize with a polynucleotide having a nucleotide sequence of SEQ ID NO: 9 under stringent conditions as long as it encodes a protein having shikimate kinase activity. Examples of stringent conditions used herein include washing one time, preferably two or three times, at salt concentrations corresponding to 1×SSC, 0.1% SDS at 65° C., preferably 0.1×SSC, 0.1% SDS at 65° C. The gene is introduced into an *Escherichia* bacterium to obtain the *Escherichia* bacterium modified to increase the expression of the gene encoding shikimate kinase. Introduction of the gene can be carried out in the same way as the introduction of the mutant tyrA gene as described above.

As described above, the *Escherichia* bacterium of the present invention can be obtained by combining a tyrA mutation with the other modifications as described above. In the breeding of the *Escherichia* bacterium of the present invention, modification to mutate a tyrA gene and modification to reduce the expression of a gene encoding prephenate dehydratase and the like may be carried out in any order.

<2> Method for Producing L-Tyrosine

The method for producing L-tyrosine of the present invention includes culturing an *Escherichia* bacterium of the present invention in a medium, producing and causing accumulation of L-tyrosine in the medium or in the bacterial cells, and collecting L-tyrosine from the medium or the bacterium cells. The culture of the *Escherichia* bacterium of the present invention can be carried out in a similar manner as a conventional culturing method for an L-tyrosine-producing bacterium. Specifically, a typical culture medium contains a carbon source, a nitrogen source, and an inorganic ion, and if necessary, an organic micronutrient such as an amino acid or a vitamin. Examples of the carbon source include glucose, sucrose, lactose, and starch-hydrolyzed solution, whey and molasses containing the sugars. Examples of the nitrogen source include ammonia in the form of ammonia gas, ammonia water, or an ammonia salt. It is preferred that the culture is carried out under aerobic conditions with the pH and temperature of the medium appropriately controlled. A considerable amount of L-tyrosine is produced, and accumulates in the culture solution after the completion of culture. A known method can be used for collecting L-tyrosine from the culture.

The present invention also provides a method for producing L-tyrosine or a derivative thereof, which includes culturing in a medium an *Escherichia* bacterium modified so that expression of the genes which encode prephenate dehydratase and a tyrosine repressor is reduced, and expression of the genes which encode PDH and shikimate kinase II is enhanced and further carrying 3-deoxy-D-arabino-heptulosonate-7-phosphate synthase which is desensitized to feedback inhibition by L-phenylalanine, producing and accumulating L-tyrosine or a derivative thereof in the medium or in the bacterial cells, and collecting L-tyrosine or a derivative thereof from the medium or the bacterial cells. The genes used for breeding the *Escherichia* bacterium in this method may be the same genes as those described above except that a wild-type PDH (tyrA) gene (e.g., a gene having a base sequence of SEQ ID NO: 1) is used instead of a mutant tyrA gene. The L-tyrosine derivative mentioned herein refers to a compound known to be produced from L-tyrosine by enhancing expression of one or more genes encoding tyrosine-metabolizing enzymes in *E. coli*, and examples thereof include melanin (European Patent No. 0547065 B1) and L-DOPA (JP 62-259589 A).

EXAMPLES

Hereinafter, the present invention will be described in detail with reference to the following non-limiting examples. The composition of the medium used in the Examples is as follows.

LB Medium:
Bactotryptone (manufactured by Difco) 10 g/L
Yeast extract (manufactured by Difco) 5 g/L
Sodium chloride 10 g/L
pH 7.0
Twenty-minute steam sterilization at 120° C. was carried out.
  LB Agar Medium:
LB medium 1L
Bacto Agar 15 g/L
Twenty-minute steam sterilization at 120° C. was carried out.
  Minimal Medium:

Glucose 0.2%
Magnesium sulfate 1 mM
Potassium dihydrogenphosphate 4.5 g/L
Sodium citrate 0.5 g/L
Ammonium sulfate 1 g/L
Disodium phosphate 10.5 g/L
Thiamine hydrochloride 5 mg/L
Ten-minute steam sterilization at 115° C. was carried out.
  Minimal Agar Medium:
Minimal medium 1L
Bacto Agar 15 g/L
Ten-minute steam sterilization at 115° C. was carried out.
  L-Tyrosine-Production Medium for *Escherichia coli*:
Glucose 40 g/L
Ammonium sulfate 16 g/L
Potassium dihydrogenphosphate 1.0 g/L
Magnesium sulfate heptahydrate 1.0 g/L
Iron(IV) sulfate heptahydrate 10 mg/L
Manganese(IV) sulfate heptahydrate 8 mg/L
Yeast extract 2.0 g/L
Official calcium carbonate 30 g/L The components were dissolved in water, except for glucose and magnesium sulfate heptahydrate, and the resulting solution was adjusted with potassium hydroxide to pH 7.0 and sterilized at 115° C. for 10 minutes. Glucose solution and magnesium sulfate heptahydrate solution were separately sterilized.

L-phenylalanine and L-tyrosine were appropriately added.

Chloramphenicol (25 mg/L) and ampicillin (100 mg/L) were added as antibiotics.

Example 1

Acquisition of Mutant tyrA Gene Encoding a Mutant PDH which is Desensitized to Feedback Inhibition (1) Acquisition of a Mutant tyrA Gene Derived from *Escherichia coli*

Chromosomal DNA was extracted from an *Escherichia coli* K-12 W3110 strain according to a standard method. Two oligonucleotide primers having the nucleotide sequence shown in SEQ ID NO: 11 and 12 were synthesized, on the basis of the nucleotide sequence of wild-type tyrA gene described in J. Mol. Biol. 180(4), 1023 (1984). One of the primers has a nucleotide sequence corresponding to the region upstream of the ORF of the tyrA gene, and the other primer has a nucleotide sequence complementary to the region downstream of the ORF of the tyrA gene. Using the primers and the chromosomal DNA as a template, PCR was carried out to obtain an approximately 1-kbp DNA fragment containing the tyrA gene. As shown in FIG. 1, this fragment was digested with EcoRI and SalI and then ligated to pSTV28 (Takara Bio Inc.), and digested with EcoRI and SalI using a Ligation Kit Ver. 2 (Takara Bio Inc.). An *Escherichia coli* K-12 JM109 strain (Takara Bio Inc.) was transformed with the ligation product and the transformed strains were selected on a LB medium containing chloramphenicol. Introduction of the tyrA gene into the obtained chloramphenicol-resistant strain was confirmed by PCR. A plasmid was isolated from the strain containing the wild-type tyrA gene and named pSTVtyrA(W).

Next, a random mutation was introduced into a wild-type tyrA gene by PCR using the Gene Morph® Random Mutagenesis Kit (STRATAGENE) and primers of SEQ ID NOs: 11 and 12, according to the manufacturer's instructions. The resulting mutated fragment was then ligated to pSTV28. The resulting plasmid containing the mutated tyrA gene fragment was used to transform *Escherichia coli* W3110 ΔtyrR, tyrA strain in which an endogenous tyrR gene and tyrA gene were disrupted. The transformed strains were selected on a minimal medium containing chloramphenicol and 0.1 mM 3-fluoro-tyrosine, and five 3-fluoro-tyrosine-resistant strains (W3110 ΔtyrR,tyrA/pSTVtyrA-1, -2, -5, -10, and -24) were tested for PDH activity. That is, the PDH activity of the selected strains was measured according to the procedure shown below.

The above-mentioned *Escherichia coli* W3110 ΔtyrR,tyrA strain can be obtained by curing the pMGAL1 plasmid (a plasmid which contains a feedback-desensitized aroG4 gene, a wild-type aroL gene, and a wild-type pheA gene) from the AJ12741 (FERM BP-4796) strain. The *Escherichia coli* AJ12741 strain was deposited at the National Institute of Bioscience and Human-Technology, Agency of Industrial Science and Technology (currently, National Institute of Advanced Industrial Science and Technology, International Patent Organism Depositary, Central 6, 1-1, Higashi 1-Chome, Tsukuba-shi, Ibaraki-ken, 305-8566, Japan) on Jun. 11, 1992 under the accession number of FERM P-13000. The original deposit was converted to an international deposit in accordance with the Budapest Treaty on Sep. 14, 1994, and given the accession number of FERM BP-4796.

(2) Measurement of PDH Activity

Figure 2:
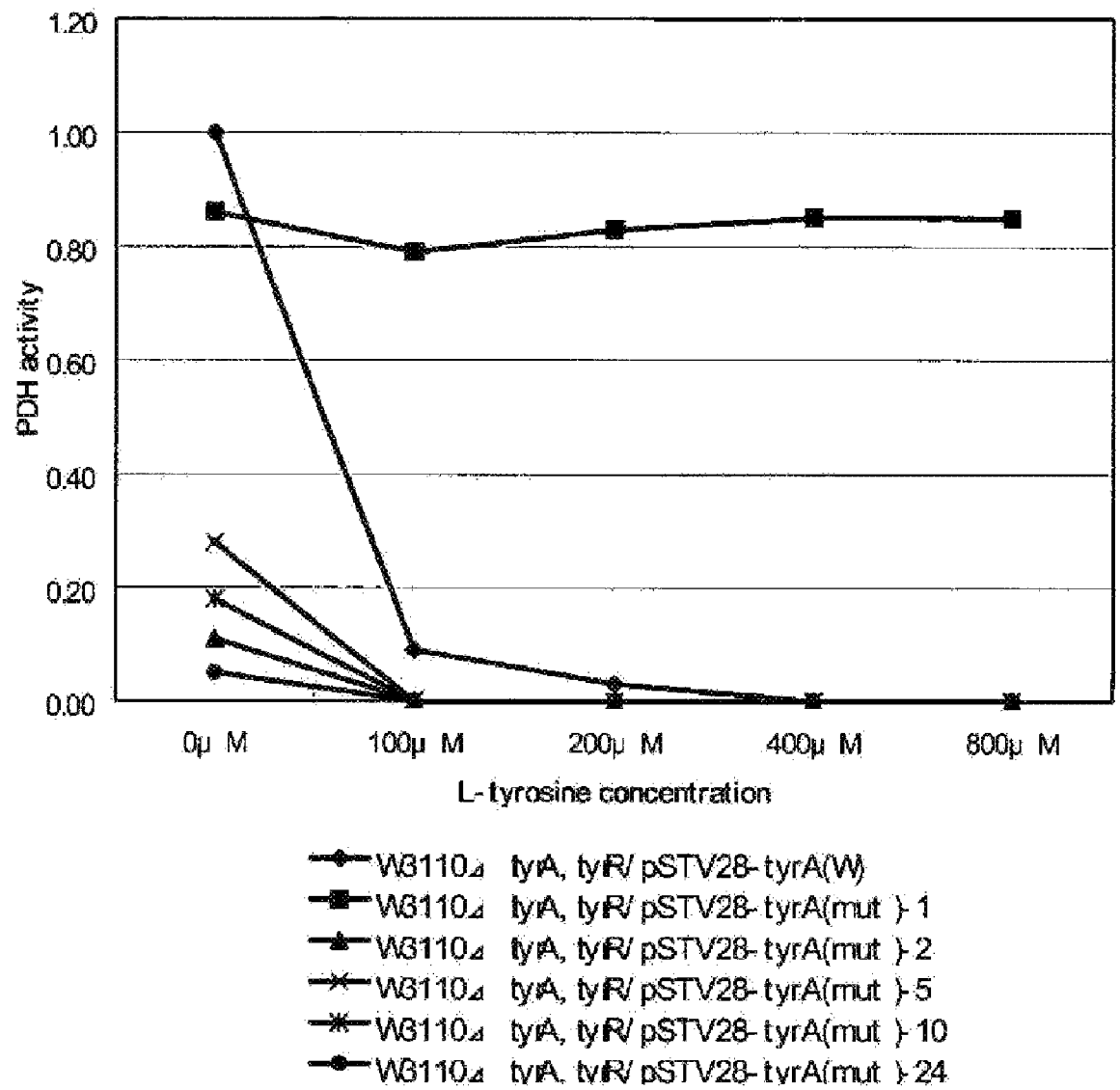
FIG. 2 shows the PDH activity at each L-tyrosine concentration.

W3110 ΔtyrR,tyrA/pSTVtyrA-1, -2, -5, -10, and -24 strains were cultured at 37° C. for 15 hours in a LB medium, respectively and each culture solution was centrifuged to collect bacterial cells. Next, after the bacterial cells were washed twice with 50 mM Tris-HCl (pH 7.5) and suspended in 50 mM Tris-HCl (pH 7.5) containing 20% glycerol on ice, a crude enzyme solution was prepared by repeating 30 second-ultrasonication 80 times. Then, the PDH activity was measured according to the method described in Biochemistry. 1990 Nov. 6; 29(44): 10245-54. That is, the enzyme reaction was performed at 30° C. for 10 minutes in 50 mM Tris-HCl (pH 7.5) containing 0.25 mM prephenate, 1 mM EDTA, 1 mM DTT, and 2 mM NAD, and the generated NADH was measured at an absorption wavelength of 340 nm. A protein assay was carried out by the Bradford method. As shown in FIG. 2, it was found that one of the selected 5 strains harbors PDH which is desensitized to feedback inhibition by L-tyrosine. PDH activity was strongly inhibited in the presence of 100 μM L-tyrosine in a strain carrying a wild-type PDH as well as strains carrying pSTVtyrA-2, -5, -10, and -24, while the W3110 ΔtyrR,tyrA/pSTVtyrA-1 strain underwent almost no inhibition even in the presence of 800 μM L-tyrosine. Hereinafter, this tyrA gene inserted into pSTVtyrA-1 is referred to as tyrA(mut).

(3) Tyrosine Production of *Escherichia coli* Strain Having a Mutant PDH which is Desensitized to Feedback Inhibition W3110 ΔtyrR,tyrA strain was transformed with pSTVtyrA (W) or pSTVtyrA(mut) and transformants were spread over LB agar medium containing 25 mg/L of chloramphenicol. Thereafter, 1 cm² of the bacterial cells grown on the medium was scraped off and inoculated in 5 ml of the above-described L-tyrosine-production medium for *Escherichia coli* containing 25 mg/L of chloramphenicol, followed by culture with shaking at 37° C. for 24 hours. After the culture, 1 ml of the culture was taken and the glucose concentration therein was measured with a Biotech Analyzer (Sakura Seiki). That is, 1 ml of the culture was centrifuged at 12,000 rpm for 2 minutes and the supernatant was diluted with water to an appropriate dilution ratio, and the glucose concentration was measured.

Figure 3:
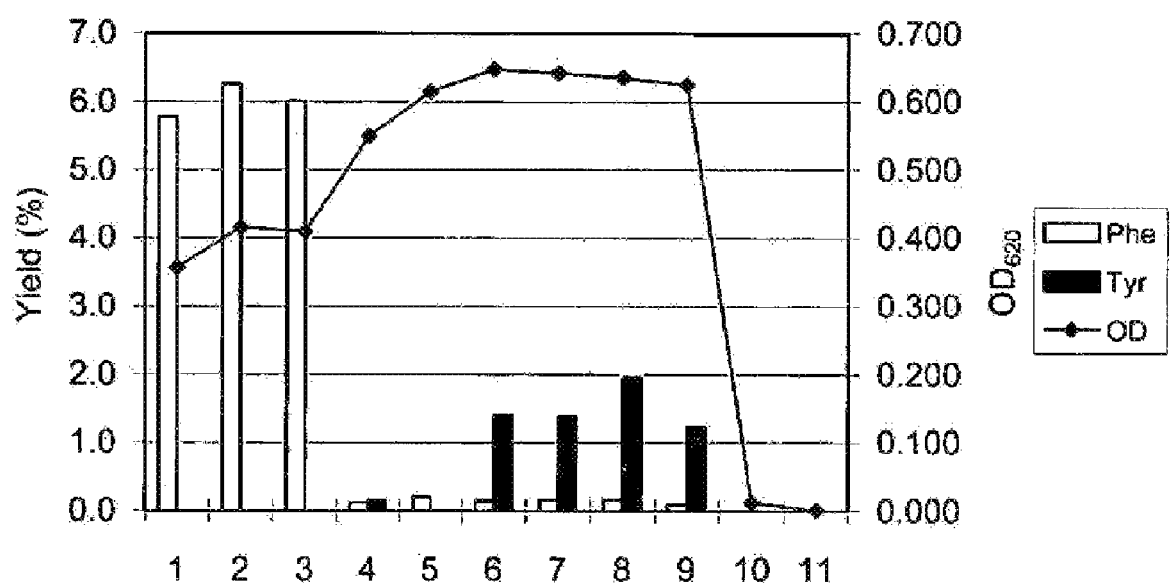
FIG. 3 shows the yields of L-tyrosine and L-phenylalanine by tyrA(mut)-introduced strain and a control strain. Each number corresponds to that in Table 1.
Figure 4:
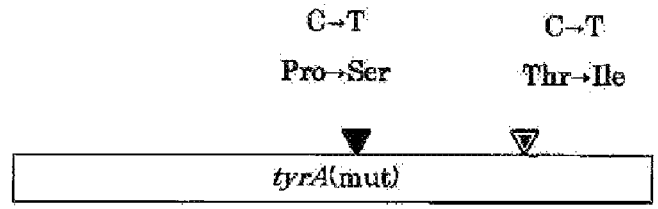
FIG. 4(A) shows positions of the mutations on the tyrA gene.
FIG. 4(B) shows the construction scheme of plasmids pSTVtyrA(T260I) or pSTVtyrA(P100S).
Figure 4:
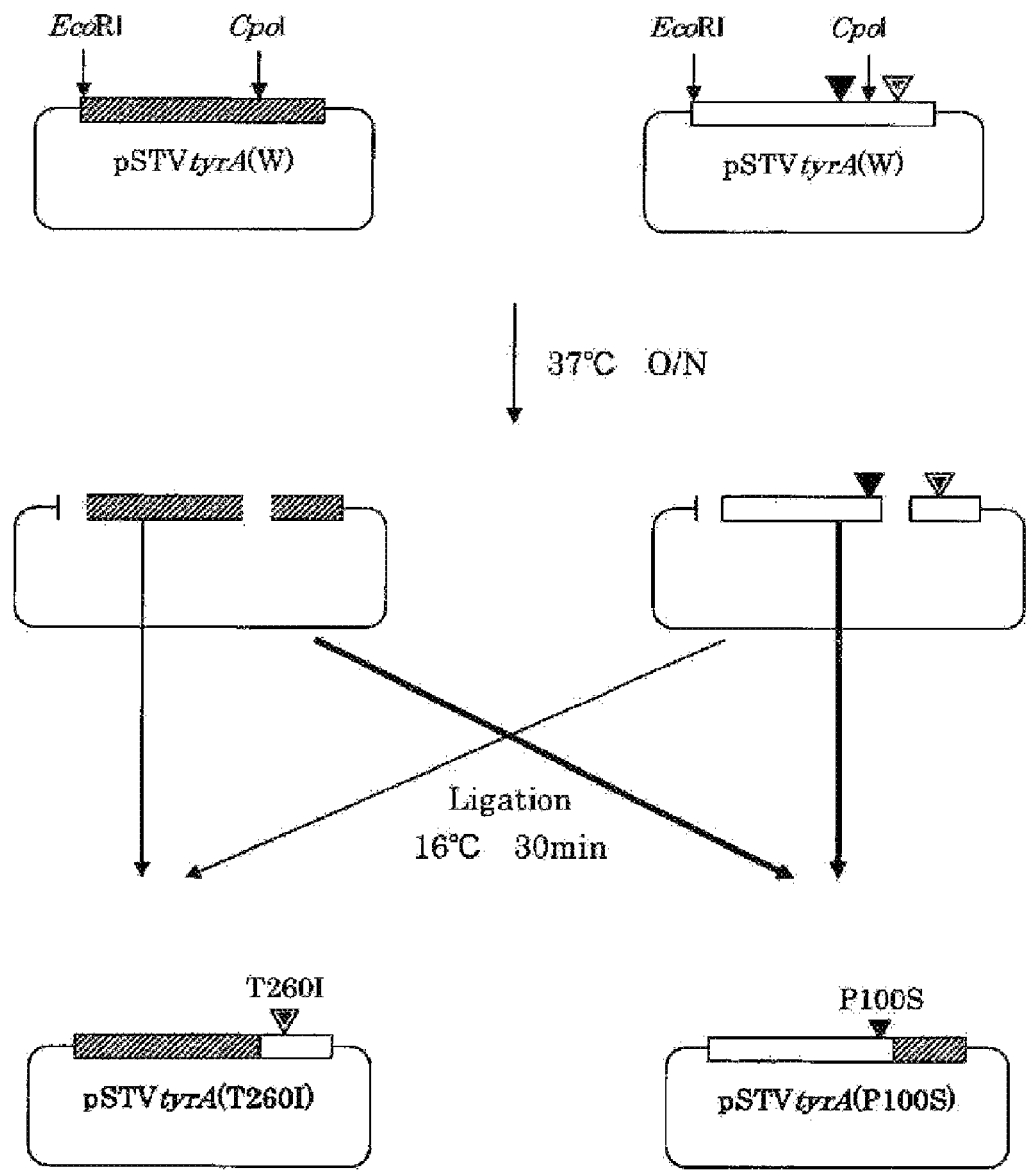

The measurement of L-tyrosine and L-phenylalanine was carried out as follows. That is, KOH was added to the remaining culture solution to a final concentration of 0.3 M and then shaken at 37° C. for 1 hour to dissolve L-tyrosine, and part of the resulting solution was removed and diluted with water to an appropriate dilution ratio and the diluted solution was passed through Ultrafree-MC 0.45 µM Filter Unit (Millipore) to remove impurities, followed by analysis using HPLC system (HITACHI). Chromolith (MERCK) was used as an HPLC column and 5% acetonitrile/0.1% trifluoroacetic acid was used as buffer. The results are shown in Table 1 and FIG. 3. It was revealed that the accumulation of L-tyrosine was increased by 8 to 10 times by the mutation in tyrA gene, which desensitizes L-tyrosine-mediated feedback inhibition of PDH activity.

sitization of the feedback inhibition of the mutant PDH, the following experiment was carried out (FIG. 4(B)). pSTVtyrA(mut) and pSTVtyrA(W) were digested with EcoRI, whose recognition site is present in the multi-cloning site upstream of the tyrA gene, and with CpoI, whose recognition site is present between the two mutation sites. The EcoRI-CpoI fragment which contains only the mutation at position 100 excised from pSTVtyrA(mut) was connected to the vector fragment of EcoRI-CpoI-digested pSTVtyrA(W), and thereby pSTVtyrA(P100S) which has a mutation only at position 100 was obtained. On the other hand, EcoRI-CpoI fragment containing no mutation excised from pSTVtyrA(W) was connected to the vector fragment of EcoRI-CpoI-digested pSTVtyrA(mut), and thereby pSTVtyrA(T260I) which has a mutation only at position 260 was obtained.

TABLE 1

| Sample | Remaining sugar g/l | OD (×1/51) | Phe g/l | Phe Yield (%) | Tyr g/l | Tyr Yield (%) |
|---|---|---|---|---|---|---|
| 1 W3110 tyrR,tyrA | 0.0 | 0.356 | 2.17 | 5.8 | | |
| 2 W3110ΔtyrR,tyrA/pSTV28 | 0.0 | 0.415 | 2.35 | 6.3 | n.d | n.d |
| 3 W3110ΔtyrR,tyrA/pSTV28 | 0.0 | 0.409 | 2.25 | 6.0 | n.d | n.d |
| 4 W3110ΔtyrR,tyrA/pSTV-tyrA(wild) | 0.1 | 0.550 | 0.05 | 0.1 | 0.06 | 0.1 |
| 5 W3110ΔtyrR,tyrA/pSTV-tyrA(wild) | 0.1 | 0.615 | 0.08 | 0.2 | n.d | n.d |
| 6 W3110ΔtyrR,tyrA/pSTV-tyrA(mut) | 0.1 | 0.647 | 0.06 | 0.2 | 0.53 | 1.4 |
| 7 W3110ΔtyrR,tyrA/pSTV-tyrA(mut) | 0.0 | 0.642 | 0.06 | 0.2 | 0.53 | 1.4 |
| 8 W3110ΔtyrR,tyrA/pSTV-tyrA(mut) | 0.1 | 0.635 | 0.06 | 0.2 | 0.74 | 2.0 |
| 9 W3110ΔtyrR,tyrA/pSTV-tyrA(mut) | 0.1 | 0.625 | 0.04 | 0.1 | 0.47 | 1.2 |
| 10 Blank | 39.5 | 0.013 | 0.00 | | 0.15 | |
| 11 Blank | 40.0 | 0.001 | 0.00 | | 0.12 | |

(4) Determination of Mutation Site of the Mutant tyrA Gene

Figure 5:
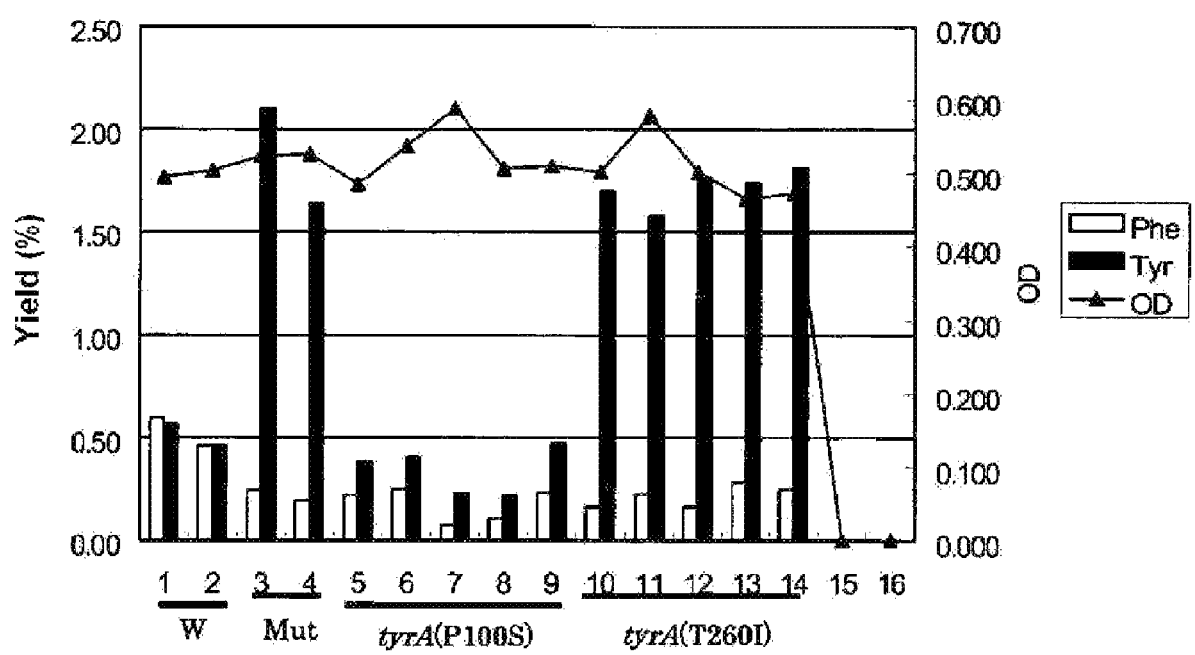
FIG. 5 shows yields of L-tyrosine and L-phenylalanine by tyrA(T260I)-introduced strain and a control strain. Each number corresponds to that in Table 2.

The nucleotide sequence of the tyrA(mut) gene was determined according to a standard method. Mutation sites in the amino acid sequence of the mutant PDH encoded by the tyrA(mut) gene are shown in FIG. 4(A). In this mutant, proline at position 100 and threonine at position 260 were replaced by serine and isoleucine, respectively. In order to confirm if either of these mutations is important to the desen- Then, W3110 ΔtyrR,tyrA strain was transformed with each of those plasmids and the resulting strains were designated W3110 ΔtyrR,tyrA/pSTVtyrA(P100S) and W3110 ΔtyrR,tyrA/pSTVtyrA(T260I), respectively. The obtained strains were cultured and L-tyrosine production was evaluated. The results are shown in Table 2 and FIG. 5. It was revealed that the amino acid substitution at position 260 of PDH is important for desensitizing feedback inhibition. Accordingly, tyrA(T260I) was used in subsequent experiments.

TABLE 2

| Sample | Remaining sugar g/l | OD (×1/51) | Phe g/l | Phe Yield (%) | Tyr g/l | Tyr Yield (%) |
|---|---|---|---|---|---|---|
| 1 W3110ΔtyrR,tyrA/pSTV-tyrA(W) | 0.0 | 0.495 | 0.20 | 0.60 | 0.19 | 0.57 |
| 2 W3110ΔtyrR,tyrA/pSTV-tyrA(W) | 0.0 | 0.504 | 0.16 | 0.46 | 0.16 | 0.46 |
| 3 W3110ΔtyrR,tyrA/pSTV-tyrA(mut) | 0.0 | 0.524 | 0.08 | 0.25 | 0.71 | 2.10 |
| 4 W3110ΔtyrR,tyrA/pSTV-tyrA(mut) | 0.0 | 0.526 | 0.07 | 0.19 | 0.55 | 1.64 |
| 5 W3110ΔtyrR,tyrA/pSTV-tyrA(P100S)-1 | 0.0 | 0.485 | 0.07 | 0.22 | 0.13 | 0.39 |
| 6 W3110ΔtyrR,tyrA/pSTV-tyrA(P100S)-2 | 0.0 | 0.537 | 0.09 | 0.25 | 0.14 | 0.41 |
| 7 W3110ΔtyrR,tyrA/pSTV-tyrA(P100S)-3 | 0.0 | 0.588 | 0.03 | 0.08 | 0.08 | 0.23 |
| 8 W3110ΔtyrR,tyrA/pSTV-tyrA(P100S)-4 | 0.0 | 0.507 | 0.04 | 0.11 | 0.07 | 0.22 |
| 9 W3110ΔtyrR,tyrA/pSTV-tyrA(P100S)-5 | 0.0 | 0.510 | 0.08 | 0.23 | 0.16 | 0.48 |
| 10 W3110ΔtyrR,tyrA/pSTV-tyrA(T260I)-1 | 0.0 | 0.502 | 0.06 | 0.17 | 0.57 | 1.70 |
| 11 W3110ΔtyrR,tyrA/pSTV-tyrA(T260I)-2 | 0.0 | 0.578 | 0.08 | 0.23 | 0.53 | 1.58 |
| 12 W3110ΔtyrR,tyrA/pSTV-tyrA(T260I)-3 | 0.0 | 0.502 | 0.06 | 0.17 | 0.60 | 1.77 |
| 13 W3110ΔtyrR,tyrA/pSTV-tyrA(T260I)-4 | 0.0 | 0.466 | 0.10 | 0.28 | 0.59 | 1.74 |
| 14 W3110ΔtyrR,tyrA/pSTV-tyrA(T260I)-5 | 0.0 | 0.473 | 0.08 | 0.25 | 0.61 | 1.81 |
| 15 Blank | 40.0 | 0.000 | 0.00 | n.d | 0.00 | n.d |
| 16 Blank | 40.0 | 0.000 | 0.00 | n.d | 0.00 | n.d |

Example 2

Acquisition of Another Mutant tyrA Gene Encoding a Mutant PDH which is Desensitized to Feedback Inhibition (1) Acquisition of Mutant tyrA Gene Derived from *Escherichia coli*

Primers for randomly inserting mutations into amino acid positions 250 to 270 of the amino acid sequence of PDH (SEQ ID NO: 2) were designed (SEQ ID NOs: 15 to 35).

Figure 8:
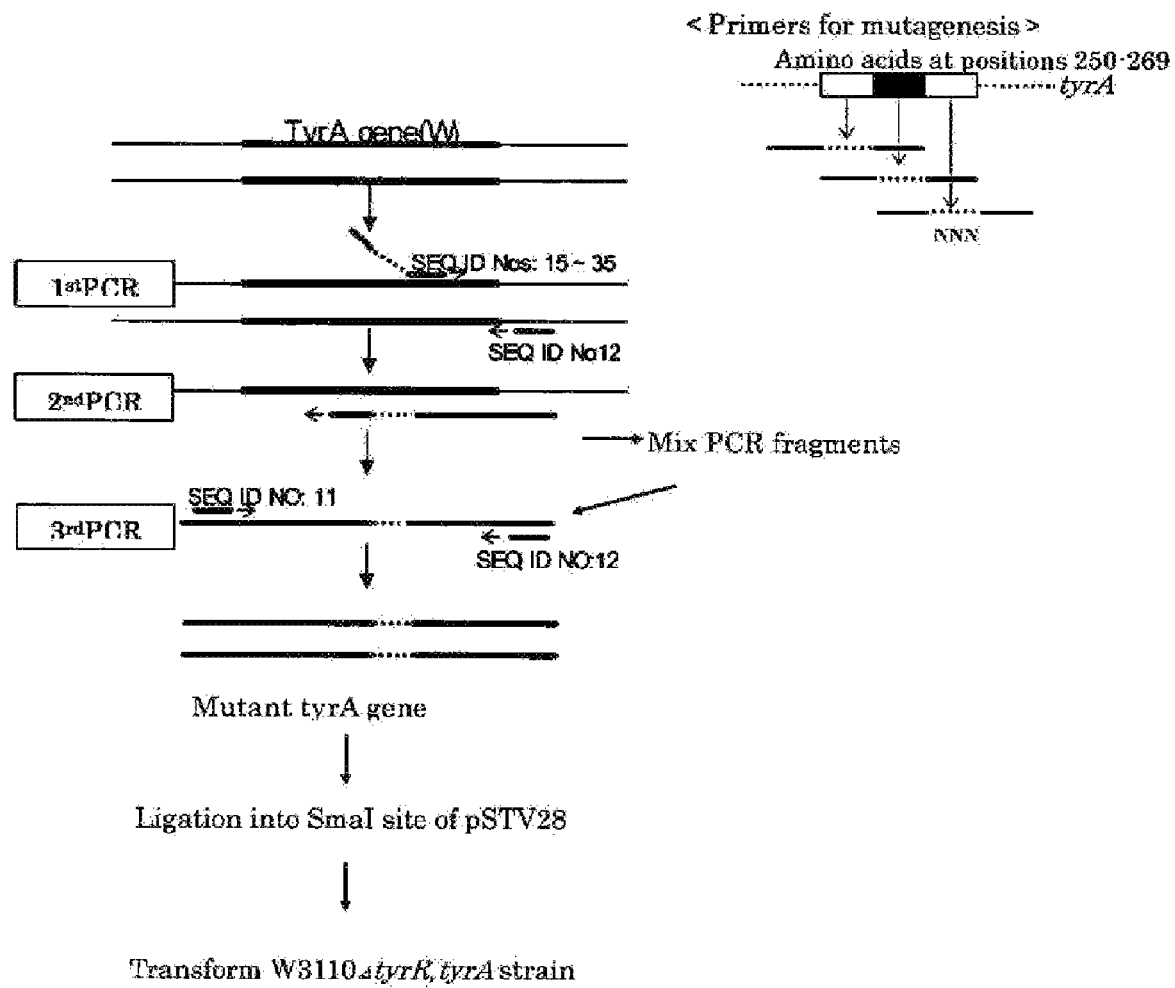
FIG. 8 shows of the PCR procedures for randomly introducing mutations into the amino acids of PDH at positions 250 to 270. Each of the primers (SEQ ID NOs: 15-35) contains a random codon (NNN) for mutating a target amino acid between the 5'-sequence and 3'-sequence each having 10-15 nucleotides and corresponding to a nucleotide sequence of the wild-type tyrA gene.

Those primers and the primers of SEQ ID NOs: 11 and 12 were used in PCR to introduce the mutations. The procedure is as follows (FIG. 8).

First PCR: any of the primers SEQ ID NOs: 15 to 35 and a T2 primer (SEQ ID NO: 12) are used to amplify a portion of the tyrA gene downstream from the mutation introduction site, from the template of pSTV tyrA(W) using pyrobest DNA polymerase (TAKARA).

Second PCR: A second PCR is carried out in the same reaction solution as that of the 1st PCR. That is, as shown in FIG. 8, the second PCR amplification proceeds after the generation of $1^{st}$ PCR product. The PCR product amplified in the 1st PCR is denatured to sense and antisense strands, and the antisense strand functions as a primer to extend toward the upstream region of tyrA gene.

<1st/2nd PCR Cycle>

96° C., 2 min.,→[94° C., 30 sec./60° C., 30 sec./72° C., 30 sec.]×20→[94° C., 1 min./37° C., 1 min./72° C., 30 sec.]×10→4° C.

Third PCR: The $3^{rd}$ PCR is performed to amplify a full length fragment of the tyrA gene which has mutations introduced using T1 (SEQ ID NO: 11) and T2 (SEQ ID NO: 12) primers, from the template of the mixture of the 2nd PCR products obtained by using each primer set.

<3rd PCR Cycle>

96° C., 2 min.,→[94° C., 30 sec./55° C., 30 sec./72° C., 1 min.]×30→4° C.

The resulting PCR fragments which contain the mutant tyrA gene were ligated to the SmaI site of pSTV28 to obtain pSTV tyrA(mut). W3110ΔtyrR,tyrA strain was transformed with the resulting plasmids. The transformants were plated on a minimal medium containing chloramphenicol and 0.1 mM 3-fluoro-tyrosine and cultured at 24 hours at 37° C. Fifty strains were selected as candidate strains from the 3-fluoro-tyrosine-resistant strains.

(2) Tyrosine Production of the 3-Fluoro-Tyrosine-Resistant Strains

The selected transformants were spread on LB agar medium containing 25 mg/L of chloramphenicol. Thereafter, 1 cm² of the bacterial cells was scraped off and inoculated in 5 ml of the above-described L-tyrosine-production medium containing 25 mg/L of chloramphenicol, followed by culture with shaking at 37° C. for 24 hours. After culture, 1 ml of the culture solution was taken and the glucose concentration in the culture solution was measured. Glucose concentration and the amount of L-tyrosine which had been produced were measured according to the method as described above. The accumulation of L-tyrosine by each transformant is shown in Table 3. This table shows that accumulation of L-tyrosine was increased by 1.5 to 5.1 times by the introduction of the mutation into tyrA gene.

(3) Determination of Mutation Sites of the tyrA Gene Encoding PDH which is Desensitized to Feedback Inhibition The nucleotide sequence of each mutant was determined according to a standard method. The codon and corresponding amino acid of the substitution site is shown in Table 3.

TABLE 3

| Mutant or Wild type | Position of amino acid substitution | Original Codon | Original Amino acid | Mutation Codon | Mutation Amino acid | Accumulation of L-tyrosine (%) |
|---|---|---|---|---|---|---|
| Mutant 1 | 253 | cag | Q | ttg | L | 1.5 |
| Mutant 2 | 255 | ctg | L | caa | Q | 1.04 |
| Mutant 3 | 255 | ctg | L | ctg | G | 1.48 |
| Mutant 4 | 258 | ttt | F | gta | V | 1.09 |
| Mutant 5 | 260 | act | T | att | I | 1.75 |
| Mutant 6 | 254/269 | gca/gaa | A/E | ggc/tac | G/Y | 2.24 |
| Mutant 7 | 257/265 | cac/ctg | H/L | tta/gca | L/A | 5.13 |
| Wild type | | | | | | 0.35 |

(4) Measurement of PDH Activity

Figure 9:
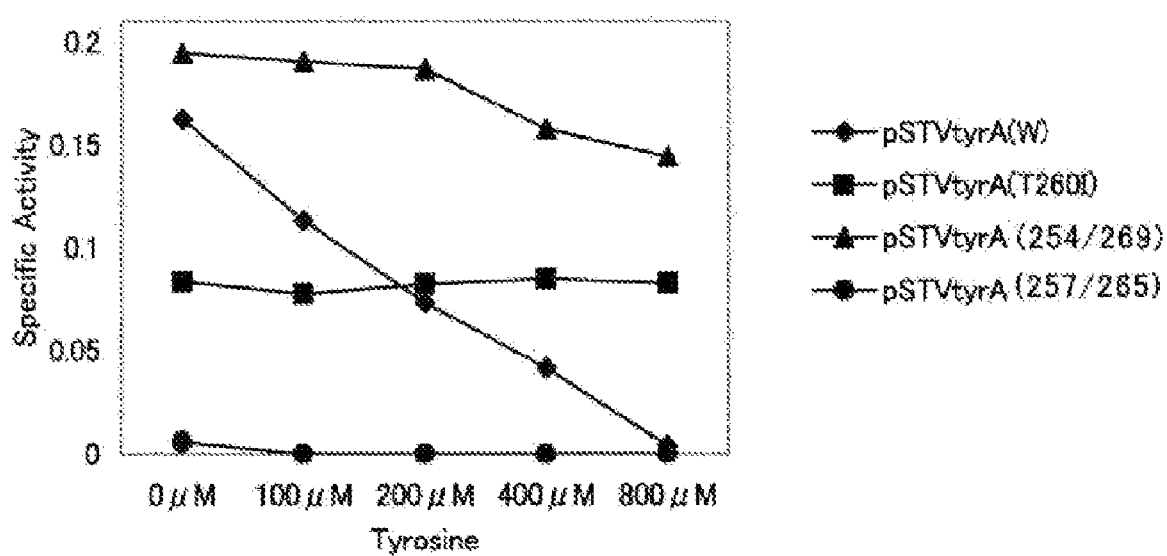
FIG. 9 shows the PDH activity of each mutant-introduced strain at each tyrosine concentration.

A strain containing mutant 7 (257/265), a strain containing mutant 6 (254/269), both shown in Table 3, and a strain containing the T260I mutation shown in Table 2 were cultured at 37° C. for 15 hours in LB medium, and after the culture, the resulting culture was centrifuged to collect bacterial cells. Then, after the bacterial cells were washed twice with 50 mM Tris-HCl (pH 7.5) and suspended in 50 mM Tris-HCl (pH 7.5) containing 20% glycerol on ice, a crude enzyme solution was prepared by repeating 30 second-ultra-sonication 80 times. PDH activity was measured according to the method described in Biochemistry. 1990 Nov. 6; 29(44): 10245-54. That is, a reaction was carried out at 30° C. for 10 minutes in 50 mM Tris-HCl (pH 7.5) containing 0.25 mM prephenate, 1 mM EDTA, 1 mM DTT, and 2 mM NAD$^+$, and NADH was measured at an absorption wavelength of 340 nm. A protein assay was carried out by the Bradford method. As shown in FIG. 9, it was found that PDH activity was strongly inhibited in the presence of 100 μM L-tyrosine in a strain harboring a wild-type PDH, while strains harboring PDH containing the T260I or 254/269 mutations underwent almost no inhibition even in the presence of 800 μM tyrosine. However, the PDH activity of the strain harboring the PDH with the 257/265 mutation could not be measured even though the L-tyrosine yield was high.

Example 3

Acquisition of Another Mutant tyrA Gene Encoding a Mutant PDH which is Desensitized to Feedback Inhibition Mutant tyrA genes were obtained similar to that described in Example 2 except that the $2^{nd}$ PCR products obtained by each primer set were not mixed but separately used as a template for $3^{rd}$ PCR. Three to ten clones of each transformant transformed with each of the 3$^{rd}$ PCR products were analyzed as a candidate for mutant tyrA-containing strains. The culture and nucleotide sequence analysis of those strains were carried out in Example 2 and the result is shown in Table 4. It was found that the mutations which cause amino acid substitutions in the region from amino acids positions 250 to 269 of PDH resulted in improved L-tyrosine yield.

TABLE 4

| | Position | original | | mutation | | Yield of Tyr (%) |
|---|---|---|---|---|---|---|
| (1) | 250 | gcg | A | ttt | F | 1.10 |
| (2) | 251 | ttt | F | agt | S | 0.60 |
| (3) | 254 | gca | A | tct | S | 0.50 |
| (4) | 254 | gca | A | ccg | P | 0.98 |
| (5) | 254 | gca | A | cct | P | 1.20 |
| (6) | 254 | gca | A | gga | G | 0.60 |
| (7) | 257 | cac | H | tac | Y | 5.50 |
| (8) | 257 | cac | H | act | T | 3.00 |
| (9) | 257 | cac | H | tca | S | 2.10 |
| (10) | 257 | cac | H | gcg | A | 3.00 |
| (11) | 258 | ttt | F | tgt | C | 0.58 |
| (12) | 258 | ttt | F | gct | A | 0.50 |
| (13) | 258 | ttt | F | ata | I | 0.74 |
| (14) | 259 | gct | A | tta | L | 1.40 |
| (15) | 259 | gct | A | gtt | V | 0.47 |
| (16) | 259 | gct | A | ata | I | 1.50 |
| (17) | 260 | act | T | ggt | G | 1.92 |
| (18) | 260 | act | T | gga | G | 1.97 |
| (19) | 260 | act | T | gct | A | 1.93 |
| (20) | 260 | act | T | gtg | V | 1.95 |
| (21) | 260 | act | T | gta | V | 1.92 |
| (22) | 260 | act | T | tgt | C | 2.32 |
| (23) | 260 | act | T | att | I | 2.97 |
| (24) | 260 | act | T | ttc | F | 3.45 |
| (25) | 260 | act | T | aat | N | 1.36 |
| (26) | 260 | act | T | tct | S | 0.45 |
| (27) | 261 | ttt | F | atg | M | 0.48 |
| (28) | 261 | ttt | F | ctc | L | 0.64 |
| (29) | 263 | tac | Y | tgt | C | 1.48 |
| (30) | 263 | tac | Y | ggg | G | 2.55 |
| (31) | 263 | tac | Y | acg | T | 2.00 |
| (32) | 263 | tac | Y | atg | M | 1.10 |
| (33) | 265 | ctg | L | aaa | K | 1.70 |
| (34) | 265 | ctg | L | att | I | 0.53 |
| (35) | 265 | ctg | L | tac | Y | 1.23 |
| (36) | 266 | cac | H | tgg | W | 3.38 |
| (37) | 266 | cac | H | tta | L | 1.16 |
| (38) | 267 | ctg | L | tat | Y | 0.50 |
| (39) | 267 | ctg | L | cat | H | 0.45 |
| (40) | 269 | gaa | E | tac | Y | 1.63 |
| (41) | 269 | gaa | E | gag | E | 0.44 |
| (42) | 269 | gaa | E | ttt | F | 1.94 |
| (43) | 269 | gaa | E | ggt | G | 2.14 |
| (44) | 269 | gaa | E | ata | I | 1.31 |
| (45) | 269 | gaa | E | ttg | L | 1.12 |
| Wild | | | | | | 0.38 |

Example 4

Disruption of pheA Gene in the W3110 ΔtyrR,tyrA Strain

The disruption of a prephenate dehydratase gene (pheA) was carried out by a method called "Red-driven integration", which was first developed by Datsenko and Wanner [Proc. Natl. Acad. Sci. USA, 2000, vol. 97, No. 12, p 6640-6645]. In this method, a DNA fragment containing a gene of interest and an antibiotic-resistant gene is used to obtain a gene-disrupted strain in one step. Based on the nucleotide sequence of a pheA gene described in J. Mol. Biol. 180(4), 1023 (1984) and a sequence of a NptII gene, which is a kanamycin-resistant gene from plasmid pCE1134 [Gene. 1982 October; 19(3): 327-36], a primer corresponding to a region in the proximity of the pheA gene and a primer complementary to a region in the proximity of the kanamycin-resistant gene were designed. The nucleotide sequences of these two primers are shown in SEQ ID NOs: 13 and 14. These primers were used to carry out PCR from the template of plasmid pCE1134.

The amplified PCR product was purified after separation by agarose gel electrophoresis, and used to transform W3110 ΔtyrR,tyrA strain containing a plasmid pKD46 having temperature-sensitive replicating ability (hereinafter referred to as W3110 ΔtyrR,tyrA/pKD46) by electroporation. The plasmid pKD46 [Proc. Natl. Acad. Sci. USA, 2000, vol. 97, No. 12, p 6640-6645] contains a DNA fragment consisting of 2,154 nucleotides derived from λ phage (GenBank/EMBL accession No. J02459, Nos. 31088 to 33241) which includes genes of a λ Red system (λ, β, exo genes) which are controlled by an arabinose-inducible ParaB promoter. The temperature-sensitive plasmid pKD46 is required for the incorporation of the PCR product into the W3100ΔtyrA,tyrA strain.

Competent cells for electroporation were prepared as follows. W3110 ΔtyrR,tyrA/pKD46 strain was cultured overnight at 30° C. in a LB medium containing 100 mg/L of ampicillin, and then diluted 100 times with 5 mL of a LB medium containing ampicillin and L-arabinose (1 mM). The diluted cells were grown at 30° C. with aeration until OD600 reached approximately 0.6. The resulting cells were then washed three times with 1 mM ice-cold HEPES (pH 7.0) and used as competent cells for electroporation. Electroporation was carried out using 50 μL of the competent cells and approximately 100 ng of the PCR product. The cells after electroporation were supplemented with 1 mL of SOC medium [Molecular Cloning: A Laboratory Manual Vol. 2, Sambrook, J. et al., Cold Spring Harbor Laboratory Press (1989)] and cultured at 37° C. for 1 hour. The resulting culture was subsequently spread on a LB agar medium and cultured at 37° C. to select kanamycin-resistant strains. Next, for curing the pKD46 plasmid, the transformants were subcultured at 37° C. on a LB agar medium with kanamycin, and the resulting colonies were tested for ampicillin-resistance to select an ampicillin-sensitive strain which was created as a result of curing pKD46 from W3110 ΔtyrR,tyrA/pKD46 strain. A mutant strain which is kanamycin-resistant and in which the pheA gene is disrupted was confirmed by PCR. That is, it was confirmed that the length of a PCR product amplified from the DNA of a pheA gene-disrupted strain (W3110ΔtyrR,tyrA,pheA::NptII) was longer than that of the wild-type W3110ΔtyrR,tyrA,pheA strain, and that the kanamycin-resistant gene was inserted within the pheA gene. Thus, it was confirmed that the pheA gene was disrupted. The pheA-disrupted strain in which the kanamycin-resistant gene was inserted was designated W3110 ΔtyrR,tyrA,pheA::Km strain.

Example 5

Figure 6:
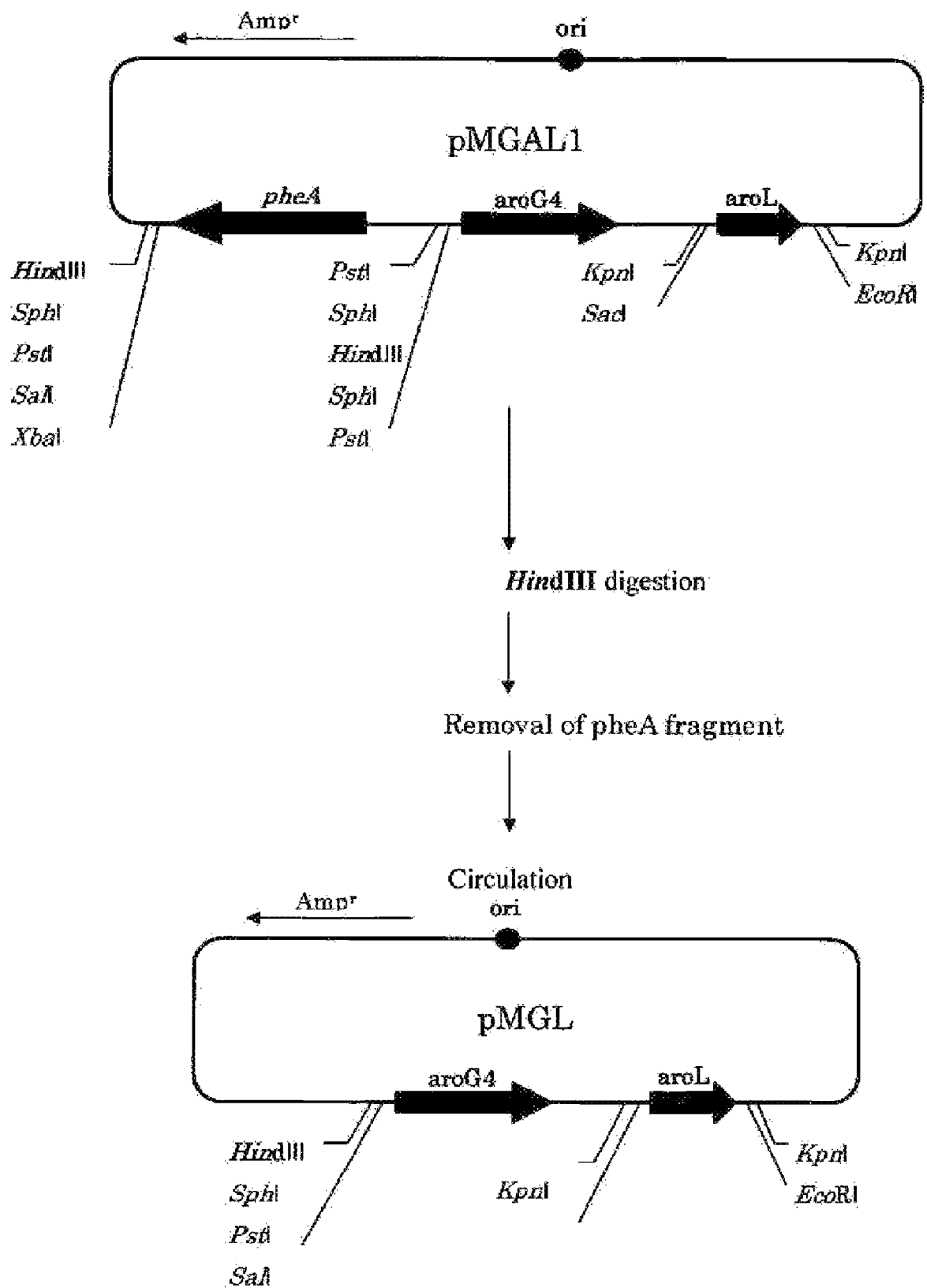
FIG. 6 shows the construction scheme of plasmid pMGL.

Production of L-Tyrosine (1) Creation of Plasmid pMGL pMGAL1 (a plasmid containing a mutant aroG4 gene resistant to feedback inhibition by L-phenylalanine, a wild-type aroL gene, and a wild-type pheA gene) which can be isolated from E. coli FERM BP-4796 strain was digested with HindIII to excise a pheA gene. The resulting plasmid, which was obtained by removing the pheA gene, was self-ligated to create a plasmid with pM119 containing only the mutant aroG4 gene and the wild-type aroL, which was designated as pMGL (FIG. 6).

(2) Creation of a Strain

The pSTVtyrA(T260I), pSTVtyrA(W) and pSTV28 as described in Example 1 were each introduced into the W3110 ΔtyrR,tyrA,pheA::Km strain obtained in Example 4 to create W3110 ΔtyrR,tyrA,pheA::Km/pSTVtyrA(T260I) strain, W3110 ΔtyrR,tyrA,pheA::Km/pSTVtyrA(W) strain, and W3110 ΔtyrR,tyrA,pheA::Km/pSTV28 strain, respectively. These strains were transformed with the above-obtained pMGL to create W3110 ΔtyrR,tyrA,pheA::Km/pMGL/pSTVtyrA(T260I) strain, W3110 ΔtyrR,tyrA,pheA::Km/pMGL/pSTVtyrA(W) strain, and W3110 ΔtyrR,tyrA,pheA::Km/pMGL/pSTV28 strain.

(3) Production of L-Tyrosine

Figure 7:
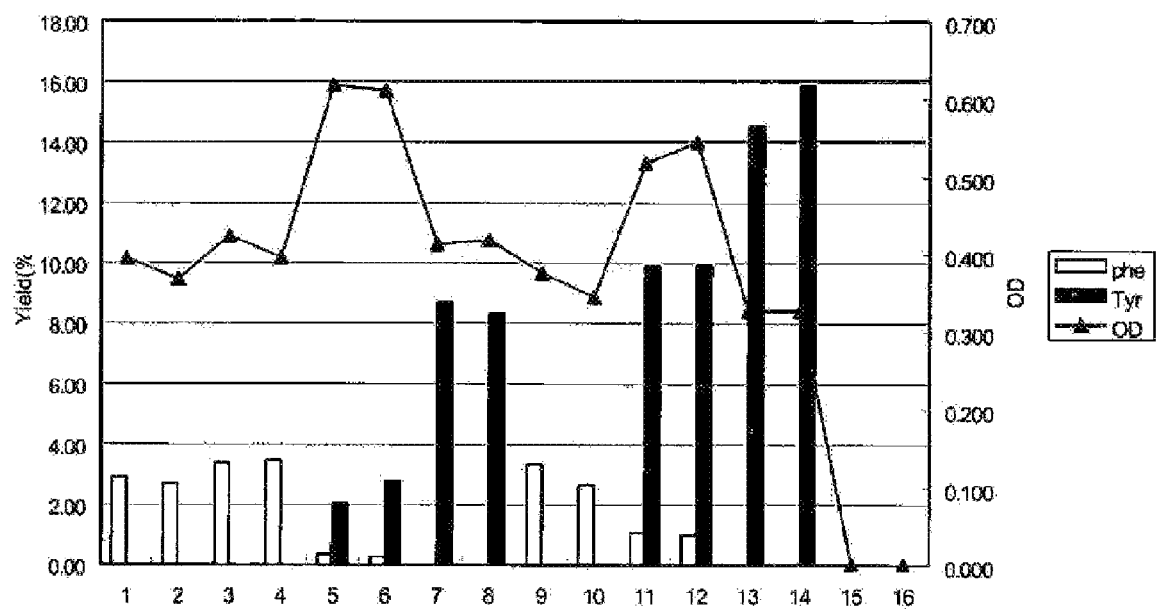
FIG. 7 shows the yields of L-tyrosine and L-phenylalanine by tyrA(T260I)-introduced strain, pMGL-introduced strain, and a control strain. Each number corresponds to that in Table 5.

Each of the transformed strains was cultured at 37° C. for 28 hours in the L-tyrosine-production medium. The results are shown in Table 5 and FIG. 7.

Analysis was carried out in the same way as in item (3) of Example 1. It was found that the introduction of the mutant tyrA gene resulted in improvement of the L-tyrosine yield, from 0.8-1.0 g/L to 3.3-3.5 g/L (approximately 5-fold improvement) in the W3110ΔtyrR,tyrA,pheA::Km strain, and from 3.9 g/L to 5.7-6.0 g/L (approximately 1.5-fold improvement) in the W3110ΔtyrR,tyrA,pheA::KmpMGL strain. Moreover, it was also found that production of L-phenylalanine as a byproduct does not occur as a result of the introduction of the mutant tyrA gene.

As shown in columns 11 and 12 of Table 5, the *Escherichia coli* strain in which the tyrR and pheA genes are disrupted and expression of the tyrA, aroL, and mutant aroG gene is enhanced, also gave a high yield of L-tyrosine.

TABLE 5

| | Sample | Remaining sugar (g/l) | OD (×1/51) | Phe g/l | Phe Yield (%) | Tyr g/l | Tyr Yield (%) |
|---|---|---|---|---|---|---|---|
| 1 | W3110ΔtyrRtyrAΔpheA::Km | 0.0 | 0.395 | 1.16 | 2.93 | 0.00 | 0.00 |
| 2 | W3110ΔtyrRtyrAΔpheA::Km | 0.0 | 0.368 | 1.07 | 2.70 | 0.00 | 0.00 |
| 3 | W3110ΔtyrRtyrAΔpheA::Km/pSTV28 | 0.0 | 0.424 | 1.35 | 3.40 | 0.00 | 0.00 |
| 4 | W3110ΔtyrRtyrAΔpheA::Km/pSTV28 | 0.0 | 0.396 | 1.38 | 3.48 | 0.00 | 0.00 |
| 5 | W3110ΔtyrRtyrAΔpheA::Km/pSTV-tyrA(wild) | 0.0 | 0.618 | 0.14 | 0.36 | 0.81 | 2.05 |
| 6 | W3110ΔtyrRtyrAΔpheA::Km/pSTV-tyrA(wild) | 0.0 | 0.611 | 0.11 | 0.27 | 1.11 | 2.79 |
| 7 | W3110ΔtyrRtyrAΔpheA::Km/pSTV-tyrA(T260I) | 0.0 | 0.413 | 0.00 | 0.00 | 3.45 | 8.70 |
| 8 | W3110ΔtyrRtyrAΔpheA::Km/pSTV-tyrA(T260I) | 0.0 | 0.419 | 0.00 | 0.00 | 3.31 | 8.35 |
| 9 | W3110ΔtyrRtyrAΔpheA::Km/pMGL | 2.0 | 0.376 | 1.26 | 3.35 | 0.00 | 0.00 |
| 10 | W3110ΔtyrRtyrAΔpheA::Km/pMGL | 0.0 | 0.345 | 1.05 | 2.65 | 0.00 | 0.00 |
| 11 | W3110ΔtyrRtyrAΔpheA::Km/pMGL/pSTV-tyrA(wild) | 0.0 | 0.518 | 0.43 | 1.08 | 3.93 | 9.91 |
| 12 | W3110ΔtyrRtyrAΔpheA::Km/pMGL/pSTV-tyrA(wild) | 0.0 | 0.545 | 0.40 | 1.01 | 3.94 | 9.93 |
| 13 | W3110ΔtyrRtyrAΔpheA::Km/pMGL/pSTV-tyrA(T260I) | 0.0 | 0.327 | 0.00 | 0.00 | 5.78 | 14.57 |
| 14 | W3110ΔtyrRtyrAΔpheA::Km/pMGL/pSTV-tyrA(T260I) | 0.0 | 0.328 | 0.00 | 0.00 | 6.30 | 15.89 |
| 15 | Blank | 41.8 | 0.000 | 0.00 | n.d | 0.00 | n.d. |
| 16 | Blank | 41.8 | 0.000 | 0.00 | n.d | 0.00 | n.d. |

While the invention has been described in detail with reference to preferred embodiments thereof, it will be apparent to one skilled in the art that various changes can be made, and equivalents employed, without departing from the scope of the invention. Each of the aforementioned documents, including the foreign priority documents, JP2004-176797 and JP2005-112484, is incorporated by reference herein in its entirety.

The invention claimed is:

1. An isolated *Escherichia* bacterium, which is able to produce L-tyrosine, comprising a prephenate dehydrogenase comprising an amino acid sequence that is not less than 95% homologous to SEQ ID NO: 2, wherein one or more of the amino acids at positions 250 to 269 of SEQ ID NO: 2 are mutated to cause the prephenate dehydrogenase to become desensitized to feedback inhibition by L-tyrosine.

2. The *Escherichia* bacterium according to claim 1, wherein mutation of the one or more of the amino acids at positions 250 to 269 is selected from the group consisting of:
   (a) the alanine at position 250 is replaced by phenylalanine,
   (b) the glutamine at position 253 is replaced by leucine,
   (c) the alanine at position 254 is replaced by serine, proline, or glycine,
   (d) the leucine at position 255 is replaced by glutamine,
   (e) the histidine at position 257 is replaced by tyrosine, threonine, serine, alanine, or leucine,
   (f) the phenylalanine at position 258 is replaced by cysteine, alanine, isoleucine, or valine,
   (g) the alanine at position 259 is replaced by leucine, valine, or isoleucine,
   (h) the threonine at position 260 is replaced by glycine, alanine, valine, cysteine, isoleucine, phenylalanine, asparagine, or serine,
   (i) the phenylalanine at position 261 is replaced by methionine or leucine,
   (j) the tyrosine at position 263 is replaced by cysteine, glycine, threonine, or methionine,
   (k) the leucine at position 265 is replaced by lysine, isoleucine, tyrosine, or alanine,
   (l) the histidine at position 266 is replaced by tryptophan or leucine,
   (m) the leucine at position 267 is replaced by tyrosine or histidine,
   (n) the glutamic acid at position 269 is replaced by tyrosine, phenylalanine, glycine, isoleucine, or leucine, and
   (o) combinations thereof.

3. The *Escherichia* bacterium according to claim 1, in which the expression of the gene encoding *E. coli* prephenate dehydratase is reduced as compared to a non-mutated *Escherichia* bacterium by a method selected from the group consisting of:
   i) disrupting the gene by homologous recombination,
   ii) modifying the promoter to reduce its function, and
   iii) combinations thereof.

4. The *Escherichia* bacterium according to claim 1, in which the expression of the gene encoding *E. coli* tyrosine repressor is reduced as compared to a non-mutated *Escherichia* bacterium by a method selected from the group consisting of:
   i) disrupting the gene by homologous recombination,
   ii) modifying the promoter to reduce its function, and
   iii) combinations thereof.

5. The *Escherichia* bacterium according to claim 1, which further comprises *E. coli* 3-deoxy-D-arabino-heptulosonate-7-phosphate synthase which is desensitized to inhibition by L-phenylalanine.

6. The *Escherichia* bacterium according to claim 1, in which the expression of the gene encoding *E. coli* shikimate kinase II is enhanced.

* * * * *

SEQUENCE LISTING

<160> NUMBER OF SEQ ID NOS: 35

<210> SEQ ID NO 1
<211> LENGTH: 1122
<212> TYPE: DNA
<213> ORGANISM: Escherichia coli
<220> FEATURE:
<221> NAME/KEY: CDS
<222> LOCATION: (1)..(1122)

<400> SEQUENCE: 1

```
atg gtt gct gaa ttg acc gca tta cgc gat caa att gat gaa gtc gat    48
Met Val Ala Glu Leu Thr Ala Leu Arg Asp Gln Ile Asp Glu Val Asp
1               5                   10                  15 aaa gcg ctg ctg aat tta tta gcg aag cgt ctg gaa ctg gtt gct gaa   96
```

|  |  |
|---|---:|
| Lys Ala Leu Leu Asn Leu Leu Ala Lys Arg Leu Glu Leu Val Ala Glu<br>            20                      25                      30 |  |
| gtg ggc gag gtg aaa agc cgc ttt gga ctg cct att tat gtt ccg gag<br>Val Gly Glu Val Lys Ser Arg Phe Gly Leu Pro Ile Tyr Val Pro Glu<br>           35                      40                      45 | 144 |
| cgc gag gca tct atg ttg gcc tcg cgt cgt gca gag gcg gaa gct ctg<br>Arg Glu Ala Ser Met Leu Ala Ser Arg Arg Ala Glu Ala Glu Ala Leu<br> 50                         55                      60 | 192 |
| ggt gta ccg cca gat ctg att gag gat gtt ttg cgt cgg gtg atg cgt<br>Gly Val Pro Pro Asp Leu Ile Glu Asp Val Leu Arg Arg Val Met Arg<br> 65                  70                      75                  80 | 240 |
| gaa tct tac tcc agt gaa aac gac aaa gga ttt aaa aca ctt tgt ccg<br>Glu Ser Tyr Ser Ser Glu Asn Asp Lys Gly Phe Lys Thr Leu Cys Pro<br>                      85                      90                      95 | 288 |
| tca ctg cgt ccg gtg gtt atc gtc ggc ggt ggc ggt cag atg gga cgc<br>Ser Leu Arg Pro Val Val Ile Val Gly Gly Gly Gly Gln Met Gly Arg<br>           100                     105                  110 | 336 |
| ctg ttc gag aag atg ctg acc ctc tcg ggt tat cag gtg cgg att ctg<br>Leu Phe Glu Lys Met Leu Thr Leu Ser Gly Tyr Gln Val Arg Ile Leu<br>           115                     120                  125 | 384 |
| gag caa cat gac tgg gat cga gcg gct gat att gtt gcc gat gcc gga<br>Glu Gln His Asp Trp Asp Arg Ala Ala Asp Ile Val Ala Asp Ala Gly<br>     130                     135                     140 | 432 |
| atg gtg att gtt agt gtg cca atc cac gtt act gag caa gtt att ggc<br>Met Val Ile Val Ser Val Pro Ile His Val Thr Glu Gln Val Ile Gly<br>145                       150                     155                  160 | 480 |
| aaa tta ccg cct tta ccg aaa gat tgt att ctg gtc gat ctg gca tca<br>Lys Leu Pro Pro Leu Pro Lys Asp Cys Ile Leu Val Asp Leu Ala Ser<br>               165                     170                  175 | 528 |
| gtg aaa aat ggg cca tta cag gcc atg ctg gtg gcg cat gat ggt ccg<br>Val Lys Asn Gly Pro Leu Gln Ala Met Leu Val Ala His Asp Gly Pro<br>               180                     185                  190 | 576 |
| gtg ctg ggg cta cac ccg atg ttc ggt ccg gac agc ggt agc ctg gca<br>Val Leu Gly Leu His Pro Met Phe Gly Pro Asp Ser Gly Ser Leu Ala<br>           195                     200                  205 | 624 |
| aag caa gtt gtg gtc tgg tgt gat gga cgt aaa ccg gaa gca tac caa<br>Lys Gln Val Val Val Trp Cys Asp Gly Arg Lys Pro Glu Ala Tyr Gln<br>               210                     215                  220 | 672 |
| tgg ttt ctg gag caa att cag gtc tgg ggc gct cgg ctg cat cgt att<br>Trp Phe Leu Glu Gln Ile Gln Val Trp Gly Ala Arg Leu His Arg Ile<br>225                       230                     235                  240 | 720 |
| agc gcc gtc gag cac gat cag aat atg gcg ttt att cag gca ctg cgc<br>Ser Ala Val Glu His Asp Gln Asn Met Ala Phe Ile Gln Ala Leu Arg<br>               245                     250                  255 | 768 |
| cac ttt gct act ttt gct tac ggg ctg cac ctg gca gaa gaa aat gtt<br>His Phe Ala Thr Phe Ala Tyr Gly Leu His Leu Ala Glu Glu Asn Val<br>                   260                     265                  270 | 816 |
| cag ctt gag caa ctt ctg gcg ctc tct tcg ccg att tac cgc ctt gag<br>Gln Leu Glu Gln Leu Leu Ala Leu Ser Ser Pro Ile Tyr Arg Leu Glu<br>           275                     280                  285 | 864 |
| ctg gcg atg gtc ggg cga ctg ttt gct cag gat ccg cag ctt tat gcc<br>Leu Ala Met Val Gly Arg Leu Phe Ala Gln Asp Pro Gln Leu Tyr Ala<br>     290                     295                     300 | 912 |
| gac atc att atg tcg tca gag cgt aat ctg gcg tta atc aaa cgt tac<br>Asp Ile Ile Met Ser Ser Glu Arg Asn Leu Ala Leu Ile Lys Arg Tyr<br>305                       310                     315                  320 | 960 |
| tat aag cgt ttc ggc gag gcg att gag ttg ctg gag cag ggc gat aag<br>Tyr Lys Arg Phe Gly Glu Ala Ile Glu Leu Leu Glu Gln Gly Asp Lys<br>                   325                     330                  335 | 1008 |

```
cag gcg ttt att gac agt ttc cgc aag gtg gag cac tgg ttc ggc gat    1056
Gln Ala Phe Ile Asp Ser Phe Arg Lys Val Glu His Trp Phe Gly Asp
            340                 345                 350 tac gca cag cgt ttt cag agt gaa agc cgc gtg tta ttg cgt cag gcg    1104
Tyr Ala Gln Arg Phe Gln Ser Glu Ser Arg Val Leu Leu Arg Gln Ala
        355                 360                 365 aat gac aat cgc cag taa                                             1122
Asn Asp Asn Arg Gln
    370
```

<210> SEQ ID NO 2
<211> LENGTH: 373
<212> TYPE: PRT
<213> ORGANISM: Escherichia coli

<400> SEQUENCE: 2

```
Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320
```

Tyr Lys Arg Phe Gly Glu Ala Ile Glu Leu Leu Glu Gln Gly Asp Lys
            325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Arg Gln Ala
            355                 360                 365

Asn Asp Asn Arg Gln
    370

<210> SEQ ID NO 3
<211> LENGTH: 1161
<212> TYPE: DNA
<213> ORGANISM: Escherichia coli
<220> FEATURE:
<221> NAME/KEY: CDS
<222> LOCATION: (1)..(1161)

<400> SEQUENCE: 3

```
atg aca tcg gaa aac ccg tta ctg gcg ctg cga gag aaa atc agc gcg      48
Met Thr Ser Glu Asn Pro Leu Leu Ala Leu Arg Glu Lys Ile Ser Ala
1               5                   10                  15 ctg gat gaa aaa tta tta gcg tta ctg gca gaa cgg cgc gaa ctg gcc      96
Leu Asp Glu Lys Leu Leu Ala Leu Leu Ala Glu Arg Arg Glu Leu Ala
                20                  25                  30 gtc gag gtg gga aaa gcc aaa ctg ctc tcg cat cgc ccg gta cgt gat     144
Val Glu Val Gly Lys Ala Lys Leu Leu Ser His Arg Pro Val Arg Asp
            35                  40                  45 att gat cgt gaa cgc gat ttg ctg gaa aga tta att acg ctc ggt aaa     192
Ile Asp Arg Glu Arg Asp Leu Leu Glu Arg Leu Ile Thr Leu Gly Lys
    50                  55                  60 gcg cac cat ctg gac gcc cat tac att act cgc ctg ttc cag ctc atc     240
Ala His His Leu Asp Ala His Tyr Ile Thr Arg Leu Phe Gln Leu Ile
65                  70                  75                  80 att gaa gat tcc gta tta act cag cag gct ttg ctc caa caa cat ctc     288
Ile Glu Asp Ser Val Leu Thr Gln Gln Ala Leu Leu Gln Gln His Leu
                85                  90                  95 aat aaa att aat ccg cac tca gca cgc atc gct ttt ctc ggc ccc aaa     336
Asn Lys Ile Asn Pro His Ser Ala Arg Ile Ala Phe Leu Gly Pro Lys
            100                 105                 110 ggt tct tat tcc cat ctt gcg gcg cgc cag tat gct gcc cgt cac ttt     384
Gly Ser Tyr Ser His Leu Ala Ala Arg Gln Tyr Ala Ala Arg His Phe
        115                 120                 125 gag caa ttc att gaa agt ggc tgc gcc aaa ttt gcc gat att ttt aat     432
Glu Gln Phe Ile Glu Ser Gly Cys Ala Lys Phe Ala Asp Ile Phe Asn
    130                 135                 140 cag gtg gaa acc ggc cag gcc gac tat gcc gtc gta ccg att gaa aat     480
Gln Val Glu Thr Gly Gln Ala Asp Tyr Ala Val Val Pro Ile Glu Asn
145                 150                 155                 160 acc agc tcc ggt gcc ata aac gac gtt tac gat ctg ctg caa cat acc     528
Thr Ser Ser Gly Ala Ile Asn Asp Val Tyr Asp Leu Leu Gln His Thr
                165                 170                 175 agc ttg tcg att gtt ggc gag atg acg tta act atc gac cat tgt ttg     576
Ser Leu Ser Ile Val Gly Glu Met Thr Leu Thr Ile Asp His Cys Leu
            180                 185                 190 ttg gtc tcc ggc act act gat tta tcc acc atc aat acg gtc tac agc     624
Leu Val Ser Gly Thr Thr Asp Leu Ser Thr Ile Asn Thr Val Tyr Ser
        195                 200                 205 cat ccg cag cca ttc cag caa tgc agc aaa ttc ctt aat cgt tat ccg     672
His Pro Gln Pro Phe Gln Gln Cys Ser Lys Phe Leu Asn Arg Tyr Pro
    210                 215                 220
```

```
cac tgg aag att gaa tat acc gaa agt acg tct gcg gca atg gaa aag        720
His Trp Lys Ile Glu Tyr Thr Glu Ser Thr Ser Ala Ala Met Glu Lys
225                 230                 235                 240 gtt gca cag gca aaa tca ccg cat gtt gct gcg ttg gga agc gaa gct        768
Val Ala Gln Ala Lys Ser Pro His Val Ala Ala Leu Gly Ser Glu Ala
                245                 250                 255 ggc ggc act ttg tac ggt ttg cag gta ctg gag cgt att gaa gca aat        816
Gly Gly Thr Leu Tyr Gly Leu Gln Val Leu Glu Arg Ile Glu Ala Asn
            260                 265                 270 cag cga caa aac ttc acc cga ttt gtg gtg ttg gcg cgt aaa gcc att        864
Gln Arg Gln Asn Phe Thr Arg Phe Val Val Leu Ala Arg Lys Ala Ile
        275                 280                 285 aac gtg tct gat cag gtt ccg gcg aaa acc acg ttg tta atg gcg acc        912
Asn Val Ser Asp Gln Val Pro Ala Lys Thr Thr Leu Leu Met Ala Thr
290                 295                 300 ggg caa caa gcc ggt gcg ctg gtt gaa gcg ttg ctg gta ctg cgc aac        960
Gly Gln Gln Ala Gly Ala Leu Val Glu Ala Leu Leu Val Leu Arg Asn
305                 310                 315                 320 cac aat ctg att atg acc cgt ctg gaa tca cgc ccg att cac ggt aat       1008
His Asn Leu Ile Met Thr Arg Leu Glu Ser Arg Pro Ile His Gly Asn
                325                 330                 335 cca tgg gaa gag atg ttc tat ctg gat att cag gcc aat ctt gaa tca       1056
Pro Trp Glu Glu Met Phe Tyr Leu Asp Ile Gln Ala Asn Leu Glu Ser
            340                 345                 350 gcg gaa atg caa aaa gca ttg aaa gag tta ggg gaa atc acc cgt tca       1104
Ala Glu Met Gln Lys Ala Leu Lys Glu Leu Gly Glu Ile Thr Arg Ser
        355                 360                 365 atg aag gta ttg ggc tgt tac cca agt gag aac gta gtg cct gtt gat       1152
Met Lys Val Leu Gly Cys Tyr Pro Ser Glu Asn Val Val Pro Val Asp
370                 375                 380 cca acc tga                                                            1161
Pro Thr
385

<210> SEQ ID NO 4
<211> LENGTH: 386
<212> TYPE: PRT
<213> ORGANISM: Escherichia coli

<400> SEQUENCE: 4

Met Thr Ser Glu Asn Pro Leu Leu Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30

Val Glu Val Gly Lys Ala Lys Leu Leu Ser His Arg Pro Val Arg Asp
        35                  40                  45

Ile Asp Arg Glu Arg Asp Leu Leu Glu Arg Leu Ile Thr Leu Gly Lys
    50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140
```

```
Gln Val Glu Thr Gly Gln Ala Asp Tyr Ala Val Pro Ile Glu Asn
145                 150                 155                 160

Thr Ser Ser Gly Ala Ile Asn Asp Val Tyr Asp Leu Leu Gln His Thr
            165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
            195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu Leu Met Ala Thr
    290                 295                 300

Gly Gln Gln Ala Gly Ala Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335

Pro Trp Glu Glu Met Phe Tyr Leu Asp Ile Gln Ala Asn Leu Glu Ser
            340                 345                 350

Ala Glu Met Gln Lys Ala Leu Lys Glu Leu Gly Glu Ile Thr Arg Ser
        355                 360                 365

Met Lys Val Leu Gly Cys Tyr Pro Ser Glu Asn Val Val Pro Val Asp
370                 375                 380

Pro Thr
385

<210> SEQ ID NO 5
<211> LENGTH: 1542
<212> TYPE: DNA
<213> ORGANISM: Escherichia coli
<220> FEATURE:
<221> NAME/KEY: CDS
<222> LOCATION: (1)..(1542)

<400> SEQUENCE: 5 atg cgt ctg gaa gtc ttt tgt gaa gac cga ctc ggt ctg acc cgc gaa      48
Met Arg Leu Glu Val Phe Cys Glu Asp Arg Leu Gly Leu Thr Arg Glu
1               5                   10                  15 tta ctc gat cta ctc gtg cta aga ggc att gat tta cgc ggt att gag      96
Leu Leu Asp Leu Leu Val Leu Arg Gly Ile Asp Leu Arg Gly Ile Glu
            20                  25                  30 att gat ccc att ggg cga atc tac ctc aat ttt gct gaa ctg gag ttt     144
Ile Asp Pro Ile Gly Arg Ile Tyr Leu Asn Phe Ala Glu Leu Glu Phe
        35                  40                  45 gag agt ttc agc agt ctg atg gcc gaa ata cgc cgt att gcg ggt gtt     192
Glu Ser Phe Ser Ser Leu Met Ala Glu Ile Arg Arg Ile Ala Gly Val
    50                  55                  60 acc gat gtg cgt act gtc ccg tgg atg cct tcc gaa cgt gag cat ctg     240
Thr Asp Val Arg Thr Val Pro Trp Met Pro Ser Glu Arg Glu His Leu
65                  70                  75                  80
```

```
gcg ttg agc gcg tta ctg gag gcg ttg cct gaa cct gtg ctc tct gtc      288
Ala Leu Ser Ala Leu Leu Glu Ala Leu Pro Glu Pro Val Leu Ser Val
             85                  90                  95 gat atg aaa agc aaa gtg gat atg gcg aac ccg gcg agc tgt cag ctt      336
Asp Met Lys Ser Lys Val Asp Met Ala Asn Pro Ala Ser Cys Gln Leu
        100                 105                 110 ttt ggg caa aaa ttg gat cgc ctg cgc aac cat acc gcc gca caa ttg      384
Phe Gly Gln Lys Leu Asp Arg Leu Arg Asn His Thr Ala Ala Gln Leu
            115                 120                 125 att aac ggc ttt aat ttt tta cgt tgg ctg gaa agc gaa ccg caa gat      432
Ile Asn Gly Phe Asn Phe Leu Arg Trp Leu Glu Ser Glu Pro Gln Asp
130                 135                 140 tcg cat aac gag cat gtc gtt att aat ggg cag aat ttc ctg atg gag      480
Ser His Asn Glu His Val Val Ile Asn Gly Gln Asn Phe Leu Met Glu
145                 150                 155                 160 att acg cct gtt tat ctt cag gat gaa aat gat caa cac gtc ctg acc      528
Ile Thr Pro Val Tyr Leu Gln Asp Glu Asn Asp Gln His Val Leu Thr
                165                 170                 175 ggt gcg gtg gtg atg ttg cga tca acg att cgt atg ggc cgc cag ttg      576
Gly Ala Val Val Met Leu Arg Ser Thr Ile Arg Met Gly Arg Gln Leu
            180                 185                 190 caa aat gtc gcc gcc cag gac gtc agc gcc ttc agt caa att gtc gcc      624
Gln Asn Val Ala Ala Gln Asp Val Ser Ala Phe Ser Gln Ile Val Ala
            195                 200                 205 gtc agc ccg aaa atg aag cat gtt gtc gaa cag gcg cag aaa ctg gcg      672
Val Ser Pro Lys Met Lys His Val Val Glu Gln Ala Gln Lys Leu Ala
        210                 215                 220 atg cta agc gcg ccg ctg ctg att acg ggt gac aca ggt aca ggt aaa      720
Met Leu Ser Ala Pro Leu Leu Ile Thr Gly Asp Thr Gly Thr Gly Lys
225                 230                 235                 240 gat ctc ttt gcc tac gcc tgc cat cag gca agc ccc aga gcg ggc aaa      768
Asp Leu Phe Ala Tyr Ala Cys His Gln Ala Ser Pro Arg Ala Gly Lys
                245                 250                 255 cct tac ctg gcg ctg aac tgt gcg tct ata ccg gaa gat gcg gtc gag      816
Pro Tyr Leu Ala Leu Asn Cys Ala Ser Ile Pro Glu Asp Ala Val Glu
            260                 265                 270 agt gaa ctg ttt ggt cat gct ccg gaa ggg aag aaa gga ttc ttt gag      864
Ser Glu Leu Phe Gly His Ala Pro Glu Gly Lys Lys Gly Phe Phe Glu
        275                 280                 285 cag gcg aac ggt ggt tcg gtg ctg ttg gat gaa ata ggg gaa atg tca      912
Gln Ala Asn Gly Gly Ser Val Leu Leu Asp Glu Ile Gly Glu Met Ser
        290                 295                 300 cca cgg atg cag gcg aaa tta ctg cgt ttc ctt aat gat ggc act ttc      960
Pro Arg Met Gln Ala Lys Leu Leu Arg Phe Leu Asn Asp Gly Thr Phe
305                 310                 315                 320 cgt cgg gtt ggc gaa gac cat gag gtg cat gtc gat gtg cgg gtg att     1008
Arg Arg Val Gly Glu Asp His Glu Val His Val Asp Val Arg Val Ile
                325                 330                 335 tgc gct acg cag aag aat ctg gtc gaa ctg gtg caa aaa ggc atg ttc     1056
Cys Ala Thr Gln Lys Asn Leu Val Glu Leu Val Gln Lys Gly Met Phe
            340                 345                 350 cgt gaa gat ctc tat tat cgt ctg aac gtg ttg acg ctc aat ctg ccg     1104
Arg Glu Asp Leu Tyr Tyr Arg Leu Asn Val Leu Thr Leu Asn Leu Pro
        355                 360                 365 ccg cta cgt gac tgt ccg cag gac atc atg ccg tta act gag ctg ttc     1152
Pro Leu Arg Asp Cys Pro Gln Asp Ile Met Pro Leu Thr Glu Leu Phe
370                 375                 380 gtc gcc cgc ttt gcc gac gag cag ggc gtg ccg cgt ccg aaa ctg gcc     1200
Val Ala Arg Phe Ala Asp Glu Gln Gly Val Pro Arg Pro Lys Leu Ala
```

-continued

```
                385                 390                 395                 400
gct gac ctg aat act gta ctt acg cgt tat gcg tgg ccg gga aat gtg       1248
Ala Asp Leu Asn Thr Val Leu Thr Arg Tyr Ala Trp Pro Gly Asn Val
                    405                 410                 415 cgg cag tta aag aac gct atc tat cgc gca ctg aca caa ctg gac ggt       1296
Arg Gln Leu Lys Asn Ala Ile Tyr Arg Ala Leu Thr Gln Leu Asp Gly
                420                 425                 430 tat gag ctg cgt cca cag gat att ttg ttg ccg gat tat gac gcc gca       1344
Tyr Glu Leu Arg Pro Gln Asp Ile Leu Leu Pro Asp Tyr Asp Ala Ala
            435                 440                 445 acg gta gcc gtg ggc gaa gat gcg atg gaa ggt tcg ctg gac gaa atc       1392
Thr Val Ala Val Gly Glu Asp Ala Met Glu Gly Ser Leu Asp Glu Ile
        450                 455                 460 acc agc cgt ttt gaa cgc tcg gta tta acc cag ctt tat cgc aat tat       1440
Thr Ser Arg Phe Glu Arg Ser Val Leu Thr Gln Leu Tyr Arg Asn Tyr
465                 470                 475                 480 ccc agc acg cgc aaa ctg gca aaa cgt ctc ggc gtt tca cat acc gcg       1488
Pro Ser Thr Arg Lys Leu Ala Lys Arg Leu Gly Val Ser His Thr Ala
                    485                 490                 495 att gcc aat aag ttg cgg gaa tat ggt ctg agt cag aag aag aac gaa       1536
Ile Ala Asn Lys Leu Arg Glu Tyr Gly Leu Ser Gln Lys Lys Asn Glu
                500                 505                 510 gag taa                                                                1542
Glu
```

<210> SEQ ID NO 6
<211> LENGTH: 513
<212> TYPE: PRT
<213> ORGANISM: Escherichia coli

<400> SEQUENCE: 6

```
Met Arg Leu Glu Val Phe Cys Glu Asp Arg Leu Gly Leu Thr Arg Glu
1               5                   10                  15

Leu Leu Asp Leu Val Leu Arg Gly Ile Asp Leu Arg Gly Ile Glu
            20                  25                  30

Ile Asp Pro Ile Gly Arg Ile Tyr Leu Asn Phe Ala Glu Leu Glu Phe
        35                  40                  45

Glu Ser Phe Ser Ser Leu Met Ala Glu Ile Arg Arg Ile Ala Gly Val
    50                  55                  60

Thr Asp Val Arg Thr Val Pro Trp Met Pro Ser Glu Arg Glu His Leu
65                  70                  75                  80

Ala Leu Ser Ala Leu Leu Glu Ala Leu Pro Glu Pro Val Leu Ser Val
                85                  90                  95

Asp Met Lys Ser Lys Val Asp Met Ala Asn Pro Ala Ser Cys Gln Leu
            100                 105                 110

Phe Gly Gln Lys Leu Asp Arg Leu Arg Asn His Thr Ala Ala Gln Leu
        115                 120                 125

Ile Asn Gly Phe Asn Phe Leu Arg Trp Leu Glu Ser Glu Pro Gln Asp
    130                 135                 140

Ser His Asn Glu His Val Val Ile Asn Gly Gln Asn Phe Leu Met Glu
145                 150                 155                 160

Ile Thr Pro Val Tyr Leu Gln Asp Glu Asn Asp Gln His Val Leu Thr
                165                 170                 175

Gly Ala Val Val Met Leu Arg Ser Thr Ile Arg Met Gly Arg Gln Leu
            180                 185                 190

Gln Asn Val Ala Ala Gln Asp Val Ser Ala Phe Ser Gln Ile Val Ala
        195                 200                 205
```

-continued

```
Val Ser Pro Lys Met Lys His Val Val Glu Gln Ala Gln Lys Leu Ala
    210                 215                 220

Met Leu Ser Ala Pro Leu Leu Ile Thr Gly Asp Thr Gly Thr Gly Lys
225                 230                 235                 240

Asp Leu Phe Ala Tyr Ala Cys His Gln Ala Ser Pro Arg Ala Gly Lys
                245                 250                 255

Pro Tyr Leu Ala Leu Asn Cys Ala Ser Ile Pro Glu Asp Ala Val Glu
            260                 265                 270

Ser Glu Leu Phe Gly His Ala Pro Glu Gly Lys Lys Gly Phe Phe Glu
        275                 280                 285

Gln Ala Asn Gly Gly Ser Val Leu Leu Asp Glu Ile Gly Glu Met Ser
    290                 295                 300

Pro Arg Met Gln Ala Lys Leu Leu Arg Phe Leu Asn Asp Gly Thr Phe
305                 310                 315                 320

Arg Arg Val Gly Glu Asp His Glu Val His Val Asp Val Arg Val Ile
                325                 330                 335

Cys Ala Thr Gln Lys Asn Leu Val Glu Leu Val Gln Lys Gly Met Phe
            340                 345                 350

Arg Glu Asp Leu Tyr Tyr Arg Leu Asn Val Leu Thr Leu Asn Leu Pro
        355                 360                 365

Pro Leu Arg Asp Cys Pro Gln Asp Ile Met Pro Leu Thr Glu Leu Phe
    370                 375                 380

Val Ala Arg Phe Ala Asp Glu Gln Gly Val Pro Arg Pro Lys Leu Ala
385                 390                 395                 400

Ala Asp Leu Asn Thr Val Leu Thr Arg Tyr Ala Trp Pro Gly Asn Val
                405                 410                 415

Arg Gln Leu Lys Asn Ala Ile Tyr Arg Ala Leu Thr Gln Leu Asp Gly
            420                 425                 430

Tyr Glu Leu Arg Pro Gln Asp Ile Leu Leu Pro Asp Tyr Asp Ala Ala
        435                 440                 445

Thr Val Ala Val Gly Glu Asp Ala Met Glu Gly Ser Leu Asp Glu Ile
    450                 455                 460

Thr Ser Arg Phe Glu Arg Ser Val Leu Thr Gln Leu Tyr Arg Asn Tyr
465                 470                 475                 480

Pro Ser Thr Arg Lys Leu Ala Lys Arg Leu Gly Val Ser His Thr Ala
                485                 490                 495

Ile Ala Asn Lys Leu Arg Glu Tyr Gly Leu Ser Gln Lys Lys Asn Glu
            500                 505                 510

Glu

<210> SEQ ID NO 7
<211> LENGTH: 1053
<212> TYPE: DNA
<213> ORGANISM: Escherichia coli
<220> FEATURE:
<221> NAME/KEY: CDS
<222> LOCATION: (1)..(1053)

<400> SEQUENCE: 7 atg aat tat cag aac gac gat tta cgc atc aaa gaa atc aaa gag tta        48
Met Asn Tyr Gln Asn Asp Asp Leu Arg Ile Lys Glu Ile Lys Glu Leu
1               5                   10                  15 ctt cct cct gtc gca ttg ctg gaa aaa ttc ccc gct act gaa aat gcc        96
Leu Pro Pro Val Ala Leu Leu Glu Lys Phe Pro Ala Thr Glu Asn Ala
            20                  25                  30
```

```
gcg aat acg gtt gcc cat gcc cga aaa gcg atc cat aag atc ctg aaa      144
Ala Asn Thr Val Ala His Ala Arg Lys Ala Ile His Lys Ile Leu Lys
         35                  40                  45 ggt aat gat gat cgc ctg ttg gtt gtg att ggc cca tgc tca att cat      192
Gly Asn Asp Asp Arg Leu Leu Val Val Ile Gly Pro Cys Ser Ile His
 50                  55                  60 gat cct gtc gcg gca aaa gag tat gcc act cgc ttg ctg gcg ctg cgt      240
Asp Pro Val Ala Ala Lys Glu Tyr Ala Thr Arg Leu Leu Ala Leu Arg
 65                  70                  75                  80 gaa gag ctg aaa gat gag ctg gaa atc gta atg cgc gtc tat ttt gaa      288
Glu Glu Leu Lys Asp Glu Leu Glu Ile Val Met Arg Val Tyr Phe Glu
                 85                  90                  95 aag ccg cgt acc acg gtg ggc tgg aaa ggg ctg att aac gat ccg cat      336
Lys Pro Arg Thr Thr Val Gly Trp Lys Gly Leu Ile Asn Asp Pro His
        100                 105                 110 atg gat aat agc ttc cag atc aac gac ggt ctg cgt ata gcc cgt aaa      384
Met Asp Asn Ser Phe Gln Ile Asn Asp Gly Leu Arg Ile Ala Arg Lys
            115                 120                 125 ttg ctg ctt gat att aac gac agc ggt ctg cca gcg gca ggt gag ttt      432
Leu Leu Leu Asp Ile Asn Asp Ser Gly Leu Pro Ala Ala Gly Glu Phe
        130                 135                 140 ctc gat atg atc acc cca caa tat ctc gct gac ctg atg agc tgg ggc      480
Leu Asp Met Ile Thr Pro Gln Tyr Leu Ala Asp Leu Met Ser Trp Gly
145                 150                 155                 160 gca att ggc gca cgt acc acc gaa tcg cag gtg cac cgc gaa ctg gca      528
Ala Ile Gly Ala Arg Thr Thr Glu Ser Gln Val His Arg Glu Leu Ala
                165                 170                 175 tca ggg ctt tct tgt ccg gtc ggc ttc aaa aat ggc acc gac ggt acg      576
Ser Gly Leu Ser Cys Pro Val Gly Phe Lys Asn Gly Thr Asp Gly Thr
            180                 185                 190 att aaa gtg gct atc gat gcc att aat gcc gcc ggt gcg ccg cac tgc      624
Ile Lys Val Ala Ile Asp Ala Ile Asn Ala Ala Gly Ala Pro His Cys
        195                 200                 205 ttc ctg tcc gta acg aaa tgg ggg cat tcg gcg att gtg aat acc agc      672
Phe Leu Ser Val Thr Lys Trp Gly His Ser Ala Ile Val Asn Thr Ser
210                 215                 220 ggt aac ggc gat tgc cat atc att ctg cgc ggc ggt aaa gag cct aac      720
Gly Asn Gly Asp Cys His Ile Ile Leu Arg Gly Gly Lys Glu Pro Asn
225                 230                 235                 240 tac agc gcg aag cac gtt gct gaa gtg aaa gaa ggg ctg aac aaa gca      768
Tyr Ser Ala Lys His Val Ala Glu Val Lys Glu Gly Leu Asn Lys Ala
                245                 250                 255 ggc ctg cca gca cag gtg atg atc gat ttc agc cat gct aac tcg tcc      816
Gly Leu Pro Ala Gln Val Met Ile Asp Phe Ser His Ala Asn Ser Ser
            260                 265                 270 aaa caa ttc aaa aag cag atg gat gtt tgt gct gac gtt tgc cag cag      864
Lys Gln Phe Lys Lys Gln Met Asp Val Cys Ala Asp Val Cys Gln Gln
        275                 280                 285 att gcc ggt ggc gaa aag gcc att att ggc gtg atg gtg gaa agc cat      912
Ile Ala Gly Gly Glu Lys Ala Ile Ile Gly Val Met Val Glu Ser His
        290                 295                 300 ctg gtg gaa ggc aat cag agc ctc gag agc ggg gag ccg ctg gcc tac      960
Leu Val Glu Gly Asn Gln Ser Leu Glu Ser Gly Glu Pro Leu Ala Tyr
305                 310                 315                 320 ggt aag agc atc acc gat gcc tgc atc ggc tgg gaa gat acc gat gct     1008
Gly Lys Ser Ile Thr Asp Ala Cys Ile Gly Trp Glu Asp Thr Asp Ala
                325                 330                 335 ctg tta cgt caa ctg gcg aat gca gta aaa gcg cgt cgc ggg taa        1053
Leu Leu Arg Gln Leu Ala Asn Ala Val Lys Ala Arg Arg Gly
            340                 345                 350
```

<210> SEQ ID NO 8
<211> LENGTH: 350
<212> TYPE: PRT
<213> ORGANISM: Escherichia coli

<400> SEQUENCE: 8

```
Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
    130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350
```

<210> SEQ ID NO 9
<211> LENGTH: 525
<212> TYPE: DNA

<213> ORGANISM: Escherichia coli
<220> FEATURE:
<221> NAME/KEY: CDS
<222> LOCATION: (1)..(525)

<400> SEQUENCE: 9

```
atg aca caa cct ctt ttt ctg atc ggg cct cgg ggc tgt ggt aaa aca      48
Met Thr Gln Pro Leu Phe Leu Ile Gly Pro Arg Gly Cys Gly Lys Thr
1               5                   10                  15 acg gtc gga atg gcc ctt gcc gat tcg ctt aac cgt cgg ttt gtc gat      96
Thr Val Gly Met Ala Leu Ala Asp Ser Leu Asn Arg Arg Phe Val Asp
                20                  25                  30 acc gat cag tgg ttg caa tca cag ctc aat atg acg gtc gcg gag atc     144
Thr Asp Gln Trp Leu Gln Ser Gln Leu Asn Met Thr Val Ala Glu Ile
            35                  40                  45 gtc gaa agg gaa gag tgg gcg gga ttt cgc gcc aga gaa acg gcg gcg     192
Val Glu Arg Glu Glu Trp Ala Gly Phe Arg Ala Arg Glu Thr Ala Ala
50                  55                  60 ctg gaa gcg gta act gcg cca tcc acc gtt atc gct aca ggc ggc ggc     240
Leu Glu Ala Val Thr Ala Pro Ser Thr Val Ile Ala Thr Gly Gly Gly
65                  70                  75                  80 att att ctg acg gaa ttt aat cgt cac ttc atg caa aat aac ggg atc     288
Ile Ile Leu Thr Glu Phe Asn Arg His Phe Met Gln Asn Asn Gly Ile
                85                  90                  95 gtg gtt tat ttg tgt gcg cca gta tca gtc ctg gtt aac cga ctg caa     336
Val Val Tyr Leu Cys Ala Pro Val Ser Val Leu Val Asn Arg Leu Gln
            100                 105                 110 gct gca ccg gaa gaa gat tta cgg cca acc tta acg gga aaa ccg ctg     384
Ala Ala Pro Glu Glu Asp Leu Arg Pro Thr Leu Thr Gly Lys Pro Leu
        115                 120                 125 agc gaa gaa gtt cag gaa gtg ctg gaa gaa cgc gat gcg cta tat cgc     432
Ser Glu Glu Val Gln Glu Val Leu Glu Glu Arg Asp Ala Leu Tyr Arg
130                 135                 140 gaa gtt gcg cat att atc atc gac gca aca aac gaa ccc agc cag gtg     480
Glu Val Ala His Ile Ile Ile Asp Ala Thr Asn Glu Pro Ser Gln Val
145                 150                 155                 160 att tct gaa att cgc agc gcc ctg gca cag acg atc aat tgt tga         525
Ile Ser Glu Ile Arg Ser Ala Leu Ala Gln Thr Ile Asn Cys
                165                 170
```

<210> SEQ ID NO 10
<211> LENGTH: 174
<212> TYPE: PRT
<213> ORGANISM: Escherichia coli

<400> SEQUENCE: 10

```
Met Thr Gln Pro Leu Phe Leu Ile Gly Pro Arg Gly Cys Gly Lys Thr
1               5                   10                  15

Thr Val Gly Met Ala Leu Ala Asp Ser Leu Asn Arg Arg Phe Val Asp
                20                  25                  30

Thr Asp Gln Trp Leu Gln Ser Gln Leu Asn Met Thr Val Ala Glu Ile
            35                  40                  45

Val Glu Arg Glu Glu Trp Ala Gly Phe Arg Ala Arg Glu Thr Ala Ala
50                  55                  60

Leu Glu Ala Val Thr Ala Pro Ser Thr Val Ile Ala Thr Gly Gly Gly
65                  70                  75                  80

Ile Ile Leu Thr Glu Phe Asn Arg His Phe Met Gln Asn Asn Gly Ile
                85                  90                  95

Val Val Tyr Leu Cys Ala Pro Val Ser Val Leu Val Asn Arg Leu Gln
            100                 105                 110
```

Ala Ala Pro Glu Glu Asp Leu Arg Pro Thr Leu Thr Gly Lys Pro Leu
        115                 120                 125

Ser Glu Glu Val Gln Glu Val Leu Glu Glu Arg Asp Ala Leu Tyr Arg
    130                 135                 140

Glu Val Ala His Ile Ile Ile Asp Ala Thr Asn Glu Pro Ser Gln Val
145                 150                 155                 160

Ile Ser Glu Ile Arg Ser Ala Leu Ala Gln Thr Ile Asn Cys
                165                 170

<210> SEQ ID NO 11
<211> LENGTH: 34
<212> TYPE: DNA
<213> ORGANISM: Artificial
<220> FEATURE:
<223> OTHER INFORMATION: primer

<400> SEQUENCE: 11
accgaattca tcaggatctg aacgggcagc tgac                               34

<210> SEQ ID NO 12
<211> LENGTH: 36
<212> TYPE: DNA
<213> ORGANISM: Artificial
<220> FEATURE:
<223> OTHER INFORMATION: primer

<400> SEQUENCE: 12
gttagtcgac atcacccgtt caatgaaggt attggg                             36

<210> SEQ ID NO 13
<211> LENGTH: 62
<212> TYPE: DNA
<213> ORGANISM: Artificial
<220> FEATURE:
<223> OTHER INFORMATION: primer

<400> SEQUENCE: 13
tggaaagatt aattacgctc ggtaaagcgc accatctgga aagcttcacg ctgccgcaag   60
ca                                                                 62

<210> SEQ ID NO 14
<211> LENGTH: 62
<212> TYPE: DNA
<213> ORGANISM: Artificial
<220> FEATURE:
<223> OTHER INFORMATION: primer

<400> SEQUENCE: 14
atacgctcca gtacctgcaa accgtacaaa gtgccgccag ggggtgggcg aagaactcca   60
gc                                                                 62

<210> SEQ ID NO 15
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 15
ctgcgccact tgctnnntt tgcttacggg ctg                                       33

<210> SEQ ID NO 16
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 16
cacgatcaga atatgnnntt tattcaggca ctg                                      33

<210> SEQ ID NO 17
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 17
gatcagaata tggcgnnnat tcaggcactg cgc                                      33

<210> SEQ ID NO 18
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 18
cagaatatgg cgtttnnnca ggcactgcgc cac                                      33

<210> SEQ ID NO 19
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 19
aatatggcgt ttattnnngc actgcgccac ttt                                      33

<210> SEQ ID NO 20
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 20
atggcgttta ttcagnnnct gcgccacttt gct                                33

<210> SEQ ID NO 21
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 21
gcgtttattc aggcannncg ccactttgct act                                33

<210> SEQ ID NO 22
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 22
tttattcagg cactgnnnca ctttgctact ttt                                33

<210> SEQ ID NO 23
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 23
attcaggcac tgcgcnnntt tgctactttt gct                                33

<210> SEQ ID NO 24
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 24
caggcactgc gccacnnngc tactttgct tac                                 33

<210> SEQ ID NO 25
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 25
gcactgcgcc actttnnnac ttttgcttac ggg                33

<210> SEQ ID NO 26
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 26
cgccactttg ctactnnngc ttacgggctg cac                33

<210> SEQ ID NO 27
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 27
cactttgcta cttttnnnta cgggctgcac ctg                33

<210> SEQ ID NO 28
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 28
tttgctactt ttgctnnngg gctgcacctg gca                33

<210> SEQ ID NO 29
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 29
gctacttttg cttacnnnct gcacctggca gaa                33

<210> SEQ ID NO 30
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c -continued

```
<400> SEQUENCE: 30 actttttgctt acgggnnnca cctggcagaa gaa                                33

<210> SEQ ID NO 31
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 31
tttgcttacg ggctgnnnct ggcagaagaa aat                                 33

<210> SEQ ID NO 32
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 32
gcttacgggc tgcacnnngc agaagaaaat gtt                                 33

<210> SEQ ID NO 33
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 33
tacgggctgc acctgnnnga agaaaatgtt cag                                 33

<210> SEQ ID NO 34
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
<223> OTHER INFORMATION: n = a, t, g or c

<400> SEQUENCE: 34
gggctgcacc tggcannnga aaatgttcag ctt                                 33

<210> SEQ ID NO 35
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (16)..(18)
```

-continued

```
<223> OTHER INFORMATION: n = a, t, g or c

<400> SEQUENCE: 35
ctgcacctgg cagaannnaa tgttcagctt gag                                    33
```